(12) United States Patent
Vestberg et al.

(10) Patent No.: US 11,844,678 B2
(45) Date of Patent: Dec. 19, 2023

(54) KITS FOR SURGICAL REPAIR OF SOFT TISSUE DEFECTS AND COMPONENTS, PACKAGING, AND METHODS OF USE THEREOF

(71) Applicant: SOFRADIM PRODUCTION, Trevoux (FR)

(72) Inventors: Robert Vestberg, Charbonniere les Bains (FR); Pierre Bailly, Caluire-et-Cuire (FR); Vit Novacek, Mesto Touskov (CZ); Amandine Radlovic, Lyons (FR)

(73) Assignee: SOFRADIM PRODUCTION, Trevoux (FR)

( * ) Notice: Subject to any disclaimer, the term of this patent is extended or adjusted under 35 U.S.C. 154(b) by 276 days.

(21) Appl. No.: 17/202,122

(22) Filed: Mar. 15, 2021

(65) Prior Publication Data

US 2021/0330436 A1    Oct. 28, 2021

(30) Foreign Application Priority Data

Apr. 23, 2020   (EP) .................................... 20315212

(51) Int. Cl.
*A61F 2/00* (2006.01)
*A61B 34/00* (2016.01)

(52) U.S. Cl.
CPC ............ *A61F 2/0063* (2013.01); *A61B 34/73* (2016.02); *A61B 2034/733* (2016.02); *A61F 2002/0072* (2013.01); *A61F 2220/0075* (2013.01)

(58) Field of Classification Search
CPC ............ A61F 2/0063; A61F 2002/0072; A61F 2220/0075; A61F 2210/009; A61B 34/73; A61B 2034/733; A61B 2017/00283; A61B 2017/00876
See application file for complete search history.

(56) References Cited

U.S. PATENT DOCUMENTS

| | | | |
|---|---|---|---|
| 7,947,054 B2 * | 5/2011 | Eldar | A61B 17/00234 606/151 |
| 2011/0184440 A1 * | 7/2011 | Saldinger | A61F 2/0063 606/151 |
| 2012/0253107 A1 | 10/2012 | Gindele et al. | |
| 2013/0331940 A1 | 12/2013 | Swanick et al. | |
| 2018/0221126 A1 * | 8/2018 | Igov | A61B 17/1285 |

FOREIGN PATENT DOCUMENTS

| | | | |
|---|---|---|---|
| WO | 2008131128 A1 | 10/2008 | |
| WO | WO-2008131128 A1 * | 10/2008 | A61B 34/70 |
| WO | 2009036094 A2 | 3/2009 | |
| WO | WO-2009036094 A2 * | 3/2009 | A61F 2/0063 |

OTHER PUBLICATIONS

Extended European Search Report issued in European Application No. 20315212.9 dated Nov. 11, 2020, 7 pages.

* cited by examiner

*Primary Examiner* — Thaddeus B Cox
*Assistant Examiner* — Marc D. Honrath
(74) *Attorney, Agent, or Firm* — WEBER ROSSELLI & CANNON LLP

(57) ABSTRACT

The present disclosure describes kits for surgical repair of soft tissue defects, including hernias. The kits include any combination of components selected from an implantable sheet, at least one loop tie, a delivery tool, a positioner, a rolling device, and a insertion member. Packaging for the kits and/or components and methods of using the kits and/or components are also provided.

16 Claims, 15 Drawing Sheets

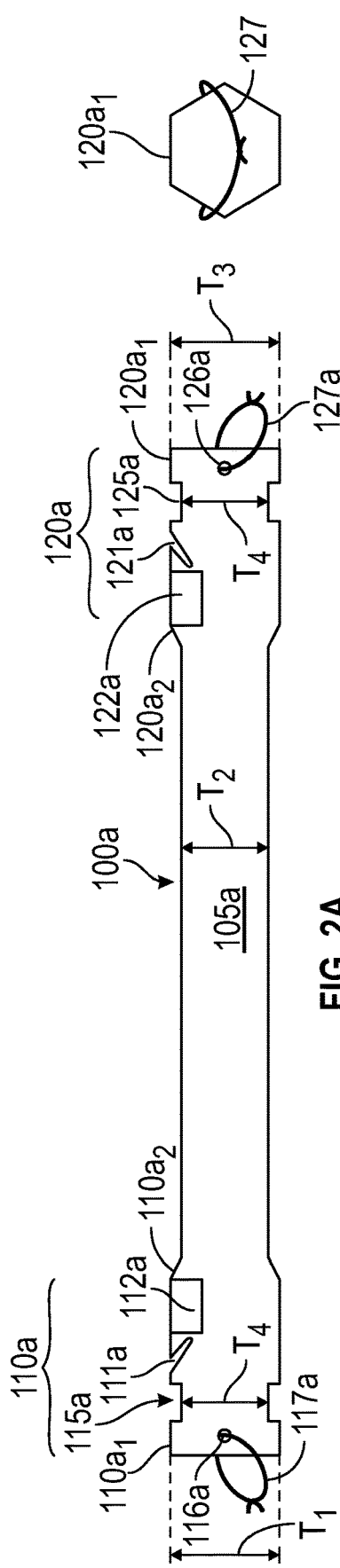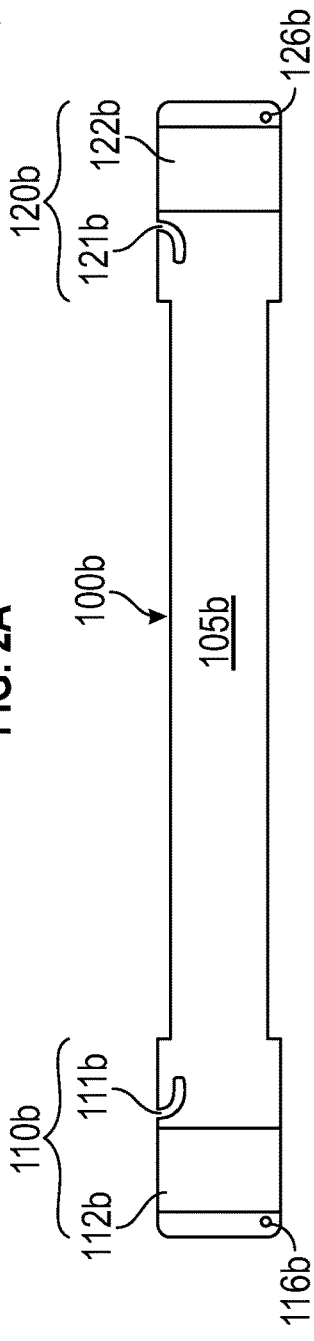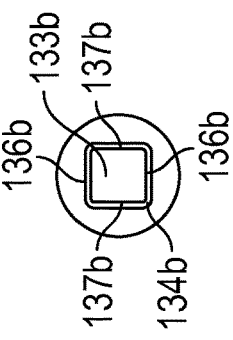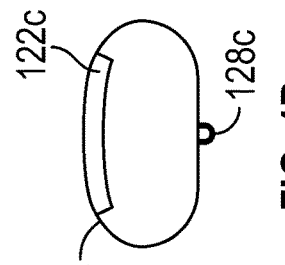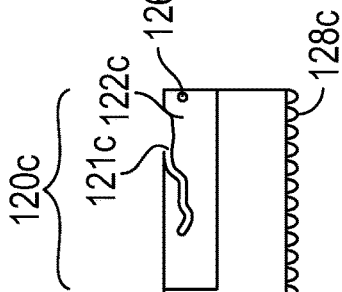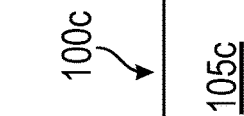

KITS FOR SURGICAL REPAIR OF SOFT TISSUE DEFECTS AND COMPONENTS, PACKAGING, AND METHODS OF USE THEREOF

CROSS-REFERENCE TO RELATED APPLICATIONS

This application claims the benefit of and priority to European Patent Application Number 20315212.9 filed on Apr. 23, 2020, the disclosure of the above-identified application is hereby incorporated by reference in its entirety.

TECHNICAL FIELD

The present disclosure describes kits for surgical repair of soft tissue defects, including hernias, and particularly to the components, packaging, and methods of use of such kits.

BACKGROUND

Various prosthetic repair materials are employed by surgeons for soft tissue repair including the repair of anatomical defects such as tissue and muscle hernias. For example, a ventral hernia in the abdominal wall is commonly repaired using an implantable sheet of biocompatible fabric, such as a knitted mesh (PARIETEX™, VERSATEX™, and the like) or a composite fabric that includes a mesh and an adhesion resistant barrier (SYMBOTEX™, PARIETENE™, and the like). The fabric is typically sutured, stapled, tacked, glued, or otherwise provisionally anchored in place over, under or within the defect. Tissue integration with the fabric, such as tissue ingrowth into and/or along the mesh fabric, eventually completes the repair. An implantable sheet of adhesion resistant barrier material, if provided alone or in combination with a fabric, prevents the growth of fibrous adhesions between the bowel (and other organs located in the abdominal cavity) and the sheet or fabric, specifically when the sheet is implanted inside the abdominal cavity (i.e. under the defect).

Various surgical techniques may be employed for soft tissue repair, including open or laparoscopic procedures. In addition, these surgical techniques may be performed directly by surgeon or with the assistance of a surgical robot. During a laparoscopic procedure, the prosthetic fabric may be routed, directly by the surgeon or with the assistance of a surgical robot, to the surgical site through a slender laparoscopic or robotic cannula. The fabric is typically collapsed, such as by rolling or folding, into a reduced configuration to facilitate its passage through the narrow cannula. Certain repairs, such as laparoscopic repair of ventral hernias, may require large sheets of prosthetic fabric that may be difficult to deliver laparoscopically, as well as difficult to properly deploy, orientate, position, or fixate following delivery.

Preparation and/or delivery of the prosthetic fabric can critically impact later steps of the surgical procedure. In laparoscopic procedures, prosthetic fabrics are typically prepared and delivered into a small operating space. This can make the deployment, orientation, positioning, and/or fixating of the fabric more difficult and more time consuming. It can also require the surgeon to dedicate one hand to simply trying to maintain the fabric in a certain position while the surgeon's second hand is trying to fixate the fabric in the tissue. This can be particularly challenging since the edges of the fabrics tend to bend or fold inside the small workspace. Mispositioning of the fixated prosthetic fabric can potentially lead to hernia recurrence.

It is an object of the present disclosure to provide kits and/or components of a kit which are designed to make preparation, insertion, deployment, orientation, positioning, and/or fixation of an implantable sheet easier, more intuitive and less time-consuming thereby rendering the surgical procedure more efficient and more effective.

It is another object of the present disclosure to provide kits and/or components of a kit which are designed to be prepared or delivered in a manner which allows a surgeon, directly or with the assistance of a surgical robot, to dedicate multiple hands to handle, deploy, orientate, position, and/or fixate the implantable sheet, during a standard laparoscopic or a robotically assisted ventral hernia repair.

SUMMARY

Surgical kits for soft tissue defect repair are described herein. The surgical kits include a combination of components selected from an implantable sheet, at least one loop tie, a delivery tool, a positioner, a rolling device, and an insertion member.

The implantable sheet, such as a surgical mesh, includes at least one loop tie, the loop tie configured to secure the implantable sheet to the delivery tool via the loop tie. The loop tie passing through a portion of the implantable sheet and extending from a bottom surface of the sheet in the form of a loop. In some embodiments, the implantable sheet includes two or more loop ties. In some embodiments, the loop tie is positioned along a central longitudinal axis of the implantable sheet.

The delivery tools described herein include a flexible rod having an elongate body extending between a proximal end portion and a distal end portion. At least one of the proximal and distal end portions of the delivery tool includes a magnetic member, a loop tie slot, or both. The magnetic member of the delivery tool is configured to attract or be attracted to a magnetic member of the positioner. The loop tie slot of the delivery tool is configured to receive and retain a loop tie extending from the implantable sheet.

In some embodiments, the proximal end portion includes a first magnetic member and a first loop tie slot defined therein. In some embodiments, the distal end portion includes a second magnetic member and a second loop tie slot defined therein.

In some embodiments, the delivery tool may further include a suture aperture extending completely through at least one of the proximal or distal end portions of the delivery tool. The suture aperture of the delivery tool is configured to receive a suture loop therethrough.

The positioners described herein are configured to magnetically engage the delivery tool from outside of the patient's body. The positioners include a handle extending between a proximal and distal end portion of the positioner. The handle of the positioner being spaced vertically from a bottom surface of the proximal and distal end portions. At least one of the proximal and distal end portions of the positioner includes a magnetic member. The magnetic member of the positioner being configured to attract or be attracted to a magnetic member of the delivery tool. In some embodiments, the proximal end portion includes a first magnetic member of the positioner. In some embodiments, the distal end portion includes a second magnetic member of the positioner.

The rolling devices described herein include a generally tubular body defining a channel therein. The channel configured to receive at least a proximal or distal end portion of the delivery tool including an implantable sheet secured thereto. The rolling devices configured to roll the sheet around the delivery tool prior to insertion into a patient. The rolling devices further include a slit. The slit of the rolling device configured to allow at least a proximal or distal end portion of the delivery tool, including a sheet secured thereto, to pass therethrough to enter the channel of the rolling device. In some embodiments, an inner surface of the tubular body includes a magnetic member configured to attract or be attracted to the magnetic member of the delivery tool. The rolling device may further include a spout, a flange, and/or a fin.

The insertion members described herein are configured to be secured to a proximal end portion of the delivery tool. The insertion members are also configured to rotate the delivery tool, when secured thereto, causing the sheet to roll around an outer surface of the delivery tool. In some embodiments, the insertion member and the rolling device are configured to be used alone or in combination, as carriers of the sheet and delivery tool.

In some embodiments, the surgical kits include an implantable sheet, such as a surgical mesh, having one or more loop ties passing therethrough, the one or more loop ties forming a loop extending from a bottom surface of the sheet. The kits also include a delivery tool including one or more magnetic members and one or more loop tie slots, the one or more loops of the loop ties being received and restrained in the one or more loop tie slots thereby connecting the sheet to the delivery tool via the loop tie. The surgical kit may also further include a positioner as described herein. The surgical kits described herein can be used for hernia repair.

In some embodiments, a method of repairing a soft tissue defect is described. The method includes combining an implantable sheet, one or more loop ties, and a magnetic delivery tool to form a sheet-tool assembly, preparing the sheet-tool assembly for insertion into a patient by forming a rolled sheet-tool assembly, inserting the rolled sheet-tool assembly into a patient, positioning the rolled sheet tool assembly underneath the soft tissue defect by positioning a magnetic positioner over the defect on an outside of the patient to magnetically engage the magnetic delivery tool; deploying and fixating the implantable sheet inside the patient, freeing the magnetic delivery tool from the sheet by removing the one or more loop ties; removing the magnetic positioner from the outer surface of the patient; and withdrawing the delivery tool from the patient. The soft tissue defect can be a ventral hernia.

In some embodiments, the methods for repairing a soft tissue defect or hernia include: combining an implantable sheet, one or more loop ties, and a delivery tool including a first and second magnetic member and one or more loop tie slots to form a sheet-tool assembly, wherein the one or more loop ties secure the sheet to the delivery tool via the one or more loop tie slots; attaching an insertion member to a proximal end portion of the delivery tool; positioning at least a distal end of the sheet-tool assembly into a rolling device; rotating the sheet around an outer surface of the delivery tool to form a rolled sheet-tool assembly; inserting the rolled sheet-tool assembly through a trocar and into a cavity of a patient, using at least one of the insertion member, the rolling device, or both; positioning a positioner including a first and second magnetic members on an outer surface of the patient's body directly over the cavity, the first and second magnetic members of the positioner magnetically engaging the first and second magnetic members of the delivery tool thereby securing the delivery tool inside the cavity to secure the sheet therebetween and beneath the soft tissue defect or hernia; deploying and fixating the implantable sheet to tissue surrounding the tissue defect; removing the positioner from the outer surface of the patient; releasing the delivery tool from the implantable sheet by removing the one or more loop ties from the implantable sheet, the delivery tool, or both; and withdrawing the delivery tool from the cavity of the patient.

BRIEF DESCRIPTION OF THE DRAWINGS

Various embodiments of the kits and/or components are described herein with reference to the drawings wherein:

FIGS. 2A-2B are a side view and an end view, respectively, of a delivery tool described in at least one embodiment herein;

FIGS. 3A-3B are a side view and an end view, respectively, of a delivery tool described in at least one embodiment herein;

FIGS. 4A-4B are a side view and an end view, respectively, of a delivery tool described in at least one embodiment herein;

DETAILED DESCRIPTION

The present disclosure describes a kit suitable for repairing various soft tissue defects, and particularly for repairing various types of hernias. The kit can include any of the following components, individually or in any combination: an implantable sheet, a loop tie, a flexible delivery tool, a positioner, a rolling device, and an insertion member. The delivery tool and the positioner each including at least one magnetic member and configured to magnetically engage each other via the respective magnetic members. In some embodiments, at least one of the rolling device or the insertion member may also include at least one magnetic member.

The term "magnetic member" as used herein is intended to refer to a magnet or a material that has magnetic properties or is attracted to a magnet. As provided in more detail hereinbelow, in embodiments wherein two different devices described herein, e.g., the delivery tool and the positioner, each include a magnetic member and are configured to magnetically engage each other, at least one of the magnetic members is a magnet.

In some embodiments, the kits described herein may include at least an implantable sheet, a first and second loop tie, a flexible magnetic delivery tool configured to be secured to a portion of the implantable sheet via the first and second loop ties, and a magnetic positioner. Such kits may further include a rolling device, an insertion member, or both.

The present disclosure further methods of treating or repairing various soft tissue defects or hernias utilizing any of the kits and/or components described herein. Methods of preparing, inserting, deploying, and/or fixating of an implantable sheet using the various components descried herein are also provided.

Figure 1:
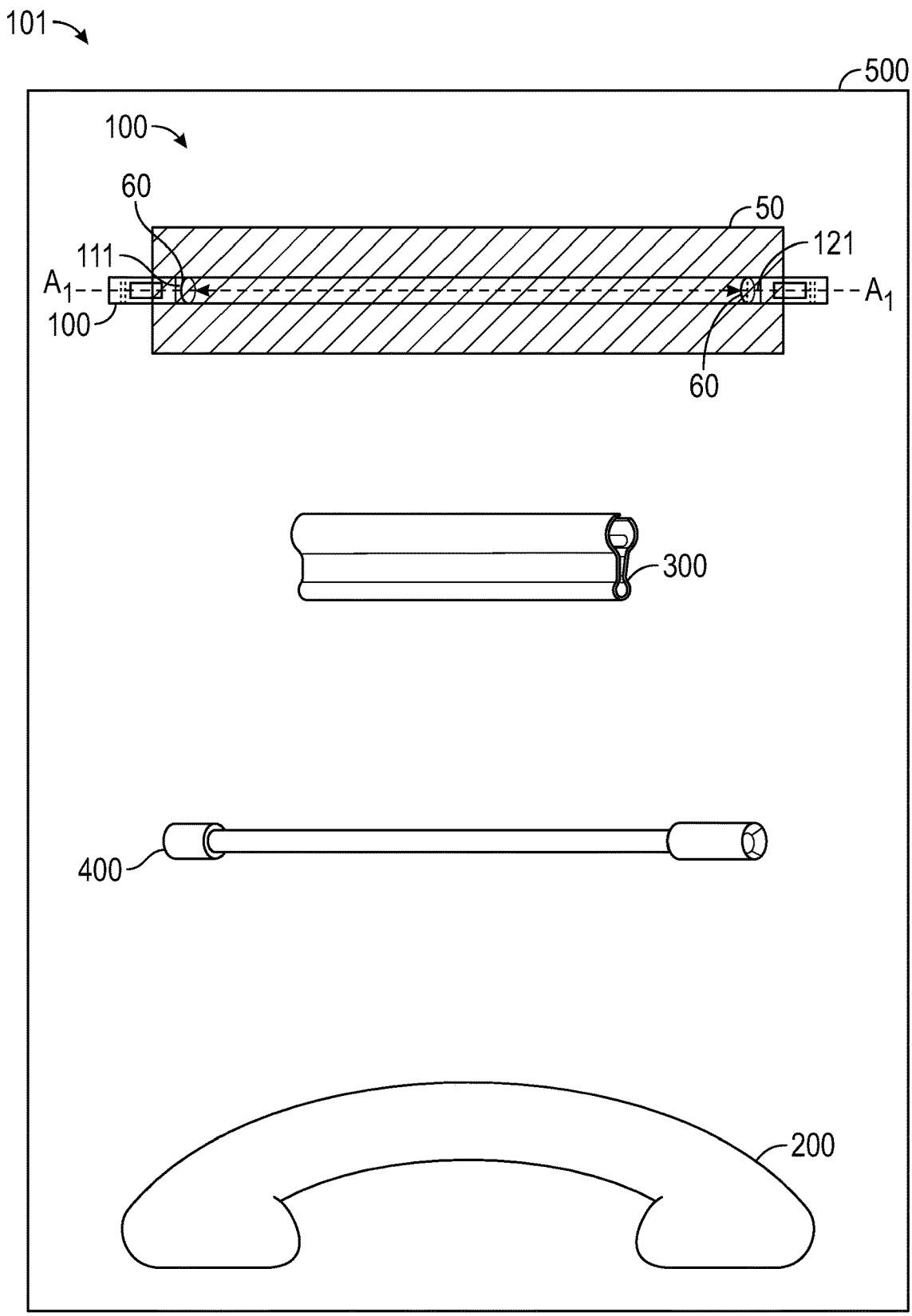
FIG. 1 is top view of a kit described in at least one embodiment herein.

In FIG. 1, a kit 101 as described in at least one embodiment herein is depicted. The kit 101 includes at least an implantable sheet 50, a delivery tool 100, and a positioner 200. The kit 101 is shown being positioned or stored in a sterile package 500 and may further include a rolling device 300, an insertion member 400, and at least one loop tie 60 extending from the sheet 50. Each of these components are provided in more detail hereinbelow.

I. Implantable Sheet

By implantable, the sheets described herein are configured to be positioned at a location within a body for any sufficient amount of time to at least temporarily treat and/or repair a soft tissue defect. In some embodiments, the biocompatible sheet is configured to be located within a portion of the abdominal cavity.

The implantable sheets described herein can be generally planar and may include any biocompatible porous or non-porous material configured to treat and/or repair a soft tissue defect. Some non-limiting examples of suitable sheets include surgical mesh, tissue scaffolds, adhesion barriers, surgical slings, surgical foams, and combinations thereof. The implantable sheet may be woven, non-woven, knitted, braided, cast, extruded, pressed, lyophilized, and the like. The implantable sheet can be bioresorbable, partially bioresorbable or non-bioresorbable.

In some embodiments, the implantable sheets described herein are surgical mesh. In the context of this application the term "mesh", "surgical mesh", or "implantable mesh" refers to an arrangement of biocompatible filaments or yarns, for example a knitted material or woven or nonwoven fibrous material, arranged in a manner to include pores within the mesh face that can encourage tissue ingrowth. The mesh can be bioresorbable, partially bioresorbable or non-bioresorbable. The mesh is generally planar or includes at least a portion which is generally planar. The mesh includes first and second opposite faces and an outer perimeter which defines a center of the mesh on each face. The mesh is also flexible enough to be rolled onto the exterior of the delivery tool and upon itself prior to insertion into a patient or a cavity defined within of a patient. The mesh can be produced from one or more layers of fabric and may optionally include an anti-adhesion barrier layer positioned on at least one portion or one side of the fabric thereby forming a composite mesh. Such meshes are well known to the person skilled in the art. The mesh can also be provided in any shape (rectangular, square, circular, oval, etc.) and size. In some embodiments, the mesh may be round or elliptical in shape when unrolled.

The implantable mesh may be a two-dimensional knitted fabric or a three-dimensional knitted fabric. In the context of the present application, the expression "two-dimensional knitted fabric" means a knitted fabric having two opposite faces linked together by stitches but having no spacers imparting a certain thickness to it: such a knitted fabric may be obtained, for example, by knitting threads on a warp or Raschel knitting machine using two guide bars. Examples of two-dimensional knitted fabrics suitable for the present invention are given in the document WO2009/071998.

In the present application, the expression "three-dimensional knitted fabric" means a knitted fabric having two opposite faces linked together by spacers imparting a significant thickness to the knitted fabric, said spacers consisting of connecting threads additional to the threads forming the two faces of the knitted fabric. Such a knitted fabric may be obtained, for example, using a double-bed Raschel knitting machine or warp knitting machine with a plurality of guide bars. Examples of knitting three-dimensional knitted fabrics suitable for the present invention are given in the documents WO99/05990, WO2009/031035, WO2009/071998.

Additionally, meshes within the scope and context of this disclosure may include fibrous biologic materials such as allografts (i.e., AlloDerm® Regenerative Tissue Matrix from Allergan), autografts, and xenografts (i.e., PERMACOL™, from Medtronic).

In some embodiments, the implantable sheets described herein are configured for use in minimally invasive surgical procedures. In some embodiments, the implantable sheets described herein are configured for use with surgical techniques including, but not limited to, TAPPS (transabdominal preperitoneal surgery), TEPS (totally extraperitoneal surgery) or IPOM (intra peritoneal onlay mesh) techniques.

In particularly useful embodiments, the implantable sheet is a surgical mesh or composite surgical mesh suitable for repairing a ventral hernia. In particularly useful embodiments, the implantable sheet is a surgical mesh or composite surgical mesh suitable for repairing a ventral hernia using any appropriate surgical technique, including but not limited to TAPPS, TEPS, or IPOM techniques.

II. Loop Tie

The loop tie is designed to connect and/or secure a portion of the delivery device, and particularly a proximal and distal end portions of the delivery device, to the implantable sheet, and particularly a proximal and distal end portions of the implantable sheet.

The loop tie can made of any absorbable or nonabsorbable material and has a length greater than its width. For example, the loop tie can be in the form of a suture, a fiber, a cable, a chord, a chain, a strip, a ribbon, a tether, a strap, or a long thin tubular mesh.

In some embodiments, the loop tie may form a closed loop. In some embodiments, the loop tie may form an open loop.

Each of the implantable sheets described herein, and particularly the two-dimensional or three-dimensional knitted fabrics, may further include at least one loop tie positioned on or near a proximal or distal end portion of at least one of the two faces of the sheet. In particular, the at least one loop tie is positioned along a central longitudinal axis $A_1$ on at least one of a proximal or distal end portions of the sheet. In particular embodiments, the sheet includes at least a first and second loop tie positioned along the central longitudinal axis $A_1$ on a proximal and distal end portion thereof, respectively.

In some embodiments, the loop tie is formed of at least one monofilament or multifilament suture which forms a loop extending from a first bottom side of the sheet a sufficient distance suitable to be secured to the delivery tool. The delivery tool includes at least one loop tie slot configured to receive the loop tie. The suture can be bioresorbable, partially bioresorbable or non-bioresorbable. The suture can be barbed or non-barbed.

In embodiments wherein the sheet includes an anti-adhesion barrier, alone or in combination with a surgical mesh, on at least a proximal or distal end portion thereof, the loop tie may also pass through the barrier.

In some embodiments, the at least one loop tie is added to the sheet prior to packaging and/or during the manufacturing process of the implantable sheet. In some embodiments, the at least one loop tie may be stored separately in the kit or package and can be added to the implantable sheet by the surgeon, either directly or with the assistance of a surgical robot, after the package is open.

In some embodiments, the implantable sheet is an implantable mesh and the at least one loop tie is a suture.

III. Delivery Tool

The kits described herein can include a delivery tool alone or in combination with at least the implantable sheet and the at least one loop tie. Some other kits include a delivery tool alone or in any combination of the components described herein.

The delivery tool includes a flexible rod having an elongate body configured to adapt to the curvature of a cavity inside a patient's body, such as the abdominal cavity. By being flexible, the delivery tool will not cause damage to tissue or organs inside the patient in the event the tool comes into direct contact with tissues or organs located inside the patient's cavity, such as the abdominal wall or organs inside an abdominal cavity. In addition, the flexible nature of the delivery tool makes it easier for the tool to enter the distal end of a trocar located inside the cavity during the withdrawal or removal process of the surgical procedure. Although flexible, the delivery tool still maintains a rigidity sufficient to generally support an implantable sheet in a rolled or unrolled configuration on an outer surface thereof.

In some embodiments, the flexible delivery tool, in its natural state, is a straight or unbent rod with the proximal and distal end portions generally 180 degrees apart. In such embodiments, the flexible delivery tool may further include the ability to bend to a curvature of at least 120 degrees when stressed, while maintaining the ability to return to its naturally straight or unbent configuration upon removal of stress. In some embodiments, the flexible delivery tool may further include the ability to bend to a curvature of at least 90 degrees when stressed, while maintaining the ability to return to its naturally straight or unbent configuration upon removal of the stress.

The delivery tool can be made of any biocompatible material displaying the appropriate flexibility characteristics. Some non-limiting examples of suitable materials include polyethylene, polypropylene, polyamides, polyurethanes, polyethylene terephthalate, polyethylene terephthalate glycol modified, polyethylene high density, polyethylene low density, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof. In addition to being biocompatible the materials used to form the delivery tool can be compatible with injection molding manufacturing processes and also compatible with standard sterilization methods, such as EtO and gamma radiation.

Some non-limiting examples of the delivery tools are provided in FIGS. 2A-7D. In some embodiments, the delivery tool is unidirectional (FIGS. 2A-4B), in that the tool extends in only one direction or includes a single axis. In some embodiments, the delivery tool is multidirectional (FIGS. 5A-7D), in that the tool extends in more than one direction or includes more than one axis.

As shown in more detail in FIGS. 2A-2B, the delivery tool 100a described herein includes a flexible rod including an elongate body 105a extending between a proximal end portion 110a and a distal end portion 120a. The proximal end portion 110a of the delivery tool 100a includes a first loop tie slot 111a defined therein, a first magnetic member 112a positioned on a proximal top surface thereof, and a first suture aperture 116a defined therethrough. The distal end portion 120a includes a second loop tie slot 121a defined therein, a second magnetic member 122a positioned on a distal top surface thereof, and a second suture aperture 126a defined therethrough.

As depicted in FIG. 2A, in some embodiments, the first loop tie slot 111a is located proximal to the first magnetic member 112a on the proximal end portion 110a of the delivery tool 100a and/or the second loop tie slot 121a is located distal to the second magnetic member 122a on the distal end portion 120a of the delivery tool 100a. The first and/or second loop tie slots 111a, 121a being configured to receive a loop tie extending from a bottom side of the implantable sheet to secure the sheet to an outer surface of the delivery tool. In some embodiments, the loop tie slot 111a, 121a defines a slot extending in a single angled plane from the outer surface of the body of the end portion (FIG. 2A).

As further depicted in FIG. 2A, in some embodiments, the loop tie slots 111a, 121a and the magnetic members 112a, 122a are positioned on a top outer portion of the delivery tool 100a. By positioning the magnetic members 112a, 122a only on a top portion of the tool 100a, along with the loop tie slots 111a, 121a, only the top of the delivery tool will be attracted to the complimentary magnetic members of the positioner (not shown in FIG. 2A-2B). This configuration allows and/or ensures the implantable sheet to be positioned on top of the delivery tool and sandwiched between the delivery tool and the patient's tissue, when the delivery tool, with the sheet secured thereto, magnetically engages the positioner positioned outside the patient's body. (see FIG. 15C).

The first and second suture apertures 116a, 126a are configured to receive a suture loop 117a, 127a therethrough. The suture loop 117a, 127a passing through and extending from the delivery tool 100a and being free of the implantable sheet. The suture loop 117a, 127a is provided to make the delivery tool 100a more accessible when inside the patient for quicker removal from the patient. The suture loop 117a, 127a also provides a larger target to grasp when trying to retrieve the delivery tool 100a, as compared to the blunt shaped distal end of the delivery tool without a suture loop.

Although each of the first and second suture apertures 116a, 126a is shown including at least one suture loop 117a, 127a, in some embodiments, only one of the suture apertures includes one or more suture loops.

As further shown in FIGS. 2A-2B, in some embodiments, at least one, if not both, of the proximal and distal end portions 110a, 120a of the delivery tool 100a may be shaped or contoured and thicker than the elongate body 105a. The proximal end portion 110a is configured to connect to a distal end portion of the insertion member (not shown in FIGS. 2A-2B). The proximal and distal end portions 110a, 120a, individually or in combination, are also configured to be used to roll or rotate the implantable sheet around the elongate body 105a of the tool 100a when a loop tie (not shown in FIGS. 2A-2B) is secured within at least one of loop tie slots 111a, 121a securing a portion of the sheet to at least one of the proximal or distal end portions 110a, 120a of the tool 100a. Once an implantable sheet is rolled around the tool 100a, the proximal end portion 110a, alone or in combination with the insertion member (not shown in FIGS. 2A-2B), can also be used to advance the delivery tool 100a in a distal direction through a trocar and into the patient or the abdominal cavity specifically (see FIG. 15A).

The shaped proximal and distal end portions 110a, 120a of the delivery tool 100a each have a thickness $T_1$, $T_3$, i.e., diameter when the end is round, greater than a thickness $T_2$ of the elongate body 105a. The shaped proximal end portion 110a of the delivery tool 100a can include any suitable shape or contour. As provided in FIG. 2B, in some embodiments, the proximal and distal end portions 110a, 120a may include a hexagonal design. In other embodiments, the proximal and distal end portions may round or elliptical (FIGS. 3A-3B and 4A-4B). Other various shapes of the proximal and distal end portions are also envisioned including, but not limited to, triangular shaped, pentagonal shaped, heptagonal shaped, octagonal shaped, star-shaped, cross-shaped, and the like.

FIG. 2A also depicts, that the delivery tool 100a, at least in some embodiments, includes a proximal and distal end portion 110a, 120a which is hexagonally-shaped and each includes a gap 115a, 125a positioned between first and second hexagonally shaped proximal end portions $110a_1$, $110a_2$, $120a_1$, $120a_2$. Each gap 115a, 125a includes a thickness $T_4$ less than the thickness $T_1$, $T_3$ of the proximal and distal end portions $110a_1$, $110a_2$, $120a_1$, $120a_2$. In some embodiments, the thickness $T_4$ of each gap 115a, 125a is greater than or generally equal to the thickness $T_2$ of the elongate body 105a.

As shown in FIGS. 3A-3B, in some embodiments, the delivery tool 100b described herein includes a flexible rod including an elongate body 105b extending between a proximal end portion 110b and a distal end portion 120b. The proximal end portion 110b of the delivery tool 100b includes a first loop tie slot 111b defined therein, a first magnetic member 112b positioned on a proximal surface thereof, and a first suture aperture 116b defined therethrough. The distal end portion 120b includes a second loop tie slot 121b defined therein, a second magnetic member 122b positioned on a distal surface thereof, and a second suture aperture 126b defined therethrough.

As depicted in FIG. 3A, in some embodiments, the first loop tie slot 111b is located distal to the first magnetic member 112b on the proximal end portion 110b of the delivery tool 100b and/or the second loop tie slot 121b is located proximal to the second magnetic member 122b on the distal end portion 120b of the delivery tool 100b. The first and/or second loop tie slot 111b, 121b being configured to receive a loop tie extending from a bottom side of the implantable sheet to secure the sheet to delivery tool. In some embodiments, the loop tie slot 111b, 121b defines a slot extending in multiple planes from the top surface of the end portion into the body of the end portion. In some embodiments, the loop tie slot 111b, 121b is a generally L-shaped slot. In some embodiments, as further depicted in FIG. 3A, each of the L-shaped loop tie slots 111b, 121b may extend toward each other and away from the magnetic members 112b, 122b.

As further depicted in FIG. 3A, in some embodiments, at least one of the first and second magnetic members 112b, 122b cover a majority, if not an entirety, of the outer surface of the proximal and/or distal end portions 110b, 120b.

The first and second suture apertures 116b, 126b are configured to receive a suture loop therethrough (not shown in FIG. 3A). In some embodiments, as shown in FIG. 3A, the suture apertures 116b, 126b may be located near the bottom of the end portions 110b, 120b.

As further shown in FIGS. 3A-3B, in some embodiments, at least one, if not both, of the proximal and distal end portions 110b, 120b of the delivery tool 100b may be shaped or contoured and thicker than the elongate body 105b. The proximal end portion 110b is configured to connect to a distal end portion of the insertion member (not shown in FIGS. 3A-3B). The proximal and distal end portions 110b, 120b, individually or in combination, are also configured to be used to roll or rotate the implantable sheet around the elongate body 105b of the tool 100b when a loop tie (not shown in FIG. 3A) is secured within at least one of loop tie slots 111b, 121b securing a portion of the sheet to at least one of the proximal or distal end portions 110b, 120b of the tool 100b. Once an implantable sheet is rolled around the tool 100b, the proximal end portion 110b, alone or in combination with the insertion member (not shown in FIG. 3A), can also be used to advance the delivery tool 100b in a distal direction through a trocar and into the patient or the abdominal cavity specifically.

In some embodiments, as shown in FIGS. 3A-3B, at least one, if not both, of the proximal and distal end portions 110b, 120b of the delivery tool 100b may be round or circular in shape and include an indentation 133b into a thickness of at least one of the proximal and distal end portions 110b, 120b. The indentation 133b is shown as generally square with rounded corners wherein the outer edge 134b of the indentation 133b further includes alternating sections of peaks 136b and valleys 137b creating a non-planar outer edge 134b of the indentation 133b. The indentation 133b provides an additional position for the insertion member to interact and lock into place with when secured to the proximal end portion 110b of the tool 100b. As further provided in more detail below, the distal end portion of the insertion member may include a protrusion configured to match or mirror the shape of the indentation 133b to further stabilize the connection between the two components (See FIGS. 12A-12B). The non-planar outer edge 134b of the indentation 133b further strengthens the interaction between the proximal end portion 110b of the tool 100b and the insertion member when attempting to manipulate or rotate the tool 100b.

In some embodiments, the shape of the indentation and the shape of the proximal end portion may be the same. In some embodiments, the shape of the indentation and the shape of the proximal end portion may be different.

As depicted, the indentation 133b may be generally square-shaped. However, other various shapes of the indentation 133b (or the matching protrusion on the insertion member) are also envisioned including, but not limited to circular-shaped, triangular-shaped, pentagonal-shaped, hexagonal-shaped, octagonal-shaped, star-shaped, cross-shaped, and the like.

Turning now to FIGS. 4A-4B, additional embodiments are described wherein the delivery tool 100c includes a proximal and distal end portion 110c, 120c which maintains a thickness equal to the thickness of the elongate body 105c. In some embodiments, at least one of the proximal and distal end portions is not shaped to have a thickness greater than the elongate body 105c. In some embodiments, the delivery tool 100c includes a generally elliptical cross-section.

As shown in FIGS. 4A-4B, in some embodiments, the delivery tool 100c described herein includes a flexible rod including an elongate body 105c extending between a proximal end portion 110c and a distal end portion 120c. The proximal end portion 110c of the delivery tool 100c includes a first loop tie slot 111c defined therein, a first magnetic member 112c positioned on a proximal top surface thereof, and a first suture aperture 116c defined therethrough. The distal end portion 120c includes a second loop tie slot 121c defined therein, a second magnetic member 122c positioned on a distal top surface thereof, and a second suture aperture 126c defined therethrough.

As depicted in FIGS. 4A and 4B, in some embodiments, the first and second magnetic members 112c, 122c, are located on the most proximal and distal ends of the tool 110c. In some embodiments, the loop tie slot 111c, 121c is positioned or defined within the area of the magnetic member 112c, 122c. In some embodiments, the loop tie slot 111c, 121c defines a sinusoidal shaped slot. In still other embodiments, the suture aperture 116c, 126c is positioned or defined within the area of the magnetic member 112c, 122c.

In addition, as further depicted in FIGS. 4A-4B, in some embodiments, the delivery tool 100c may include crenulations 118c, 128c extending outwardly from a bottom outer surface of the proximal and distal end portions 110c, 120c. The crenulations 118c, 128c are configured to engage the implantable sheet, and particularly the open pores of the sheet, during rolling to improve the ability of the delivery tool 100c to tightly roll the sheet thereon. The crenulations 118c, 128c are shown as generally round and may include a point at a tip thereof. It is envisioned that the crenulations can be of any shape useful for engaging the sheet during rolling.

Although shown on only the end portions of the delivery tool, it is envisioned that the crenulations also may be positioned on an outer surface of at least a portion of the elongate body of the delivery tool.

Examples of multi-directional delivery tools are provided in FIGS. 5A-7D. In some embodiments, the multidirectional delivery tools are configured to transition between a generally unidirectional configuration and a multidirectional configuration. In some embodiments, the multidirectional delivery tools are configured to be unidirectional any time prior to deployment of the implantable sheet so that the delivery tool can be easily passed into the patient's body through a trocar. In some embodiments, the multidirectional delivery tools are configured to be multidirectional throughout.

Figure 5A:
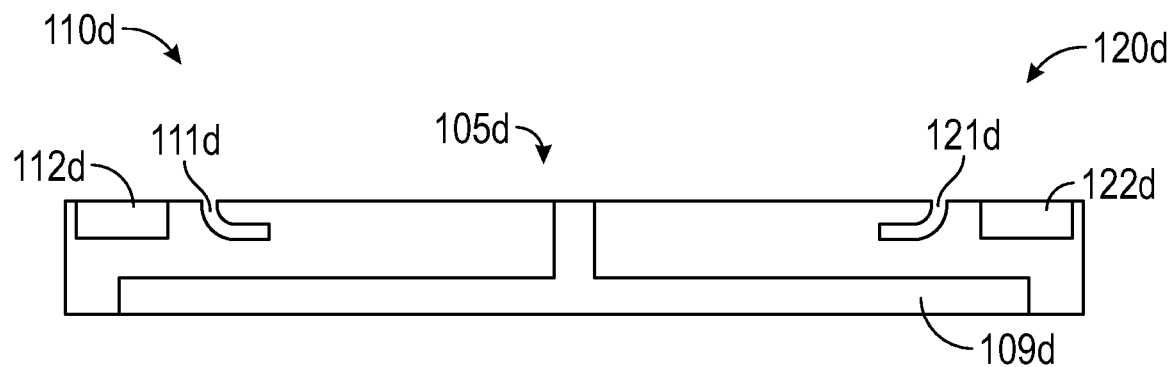
FIG. 5A is a side view of a delivery tool in a unidirectional configuration as described in at least one embodiment herein.
Figure 5B:
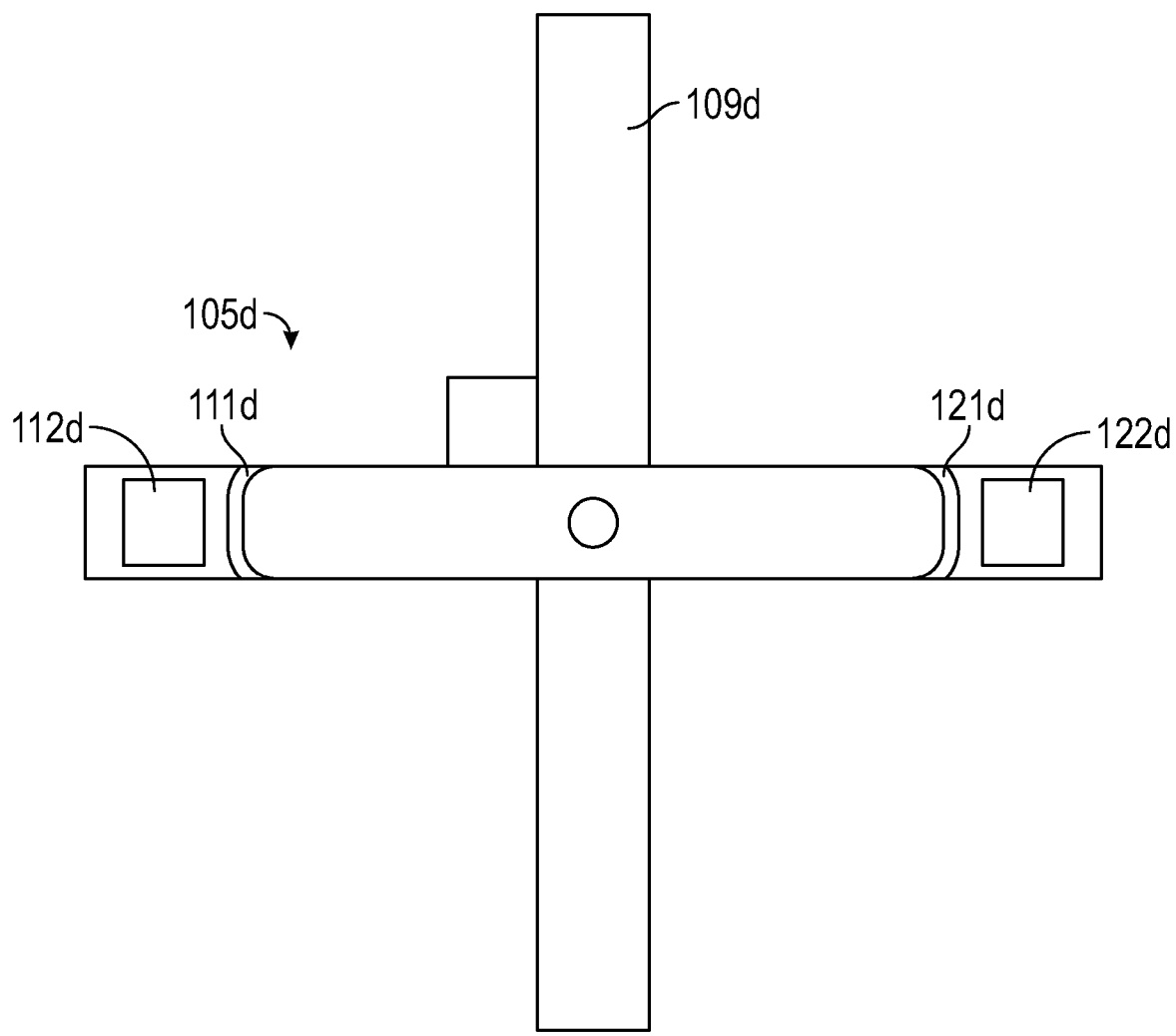
FIG. 5B is a top view of the delivery tool depicted in FIG. 5A in a multidirectional configuration as described in at least one embodiment herein.

In FIGS. 5A and 5B, the multi-directional magnetic delivery tool 100d includes first and second magnetic members 112d, 122d, first and second loop tie slots 111d, 121d, positioned on first and second distal end portions 110d, 120d, with elongate body 105d extending therebetween and further including at least one pivotable arm 109d configured to pivot or rotate from a first aligned position, wherein the arm 109d is vertically aligned with the elongate body 105d (FIG. 5A), to a second transverse position, wherein the arm rotates about ninety degrees to be perpendicular to the elongate body 105d (FIG. 5B). It is envisioned that in some embodiments, the arm 109d can be configured to rotate from about 1 to about 360 degrees in either direction as needed. In some embodiments, the arm is pivoted or rotated manually by the surgeon inside the patient's body. In some embodiments, the arm maintains and displays a natural bias to pivot or rotate away from the elongate body. In such embodiments, the combination of the rolling device and/or the rolled implantable sheet may be used to prevent the naturally biased arm from rotating or pivoting away from the elongated body prematurely.

Figure 6A:
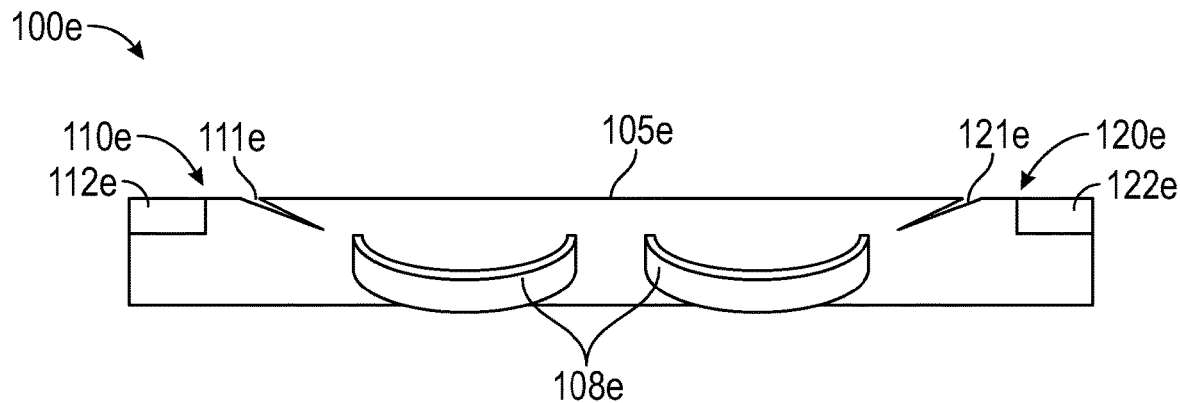
FIGS. 6A and 6B include a side view and a top view, respectively, of a multidirectional delivery tool described in at least one embodiment herein.
Figure 6B:
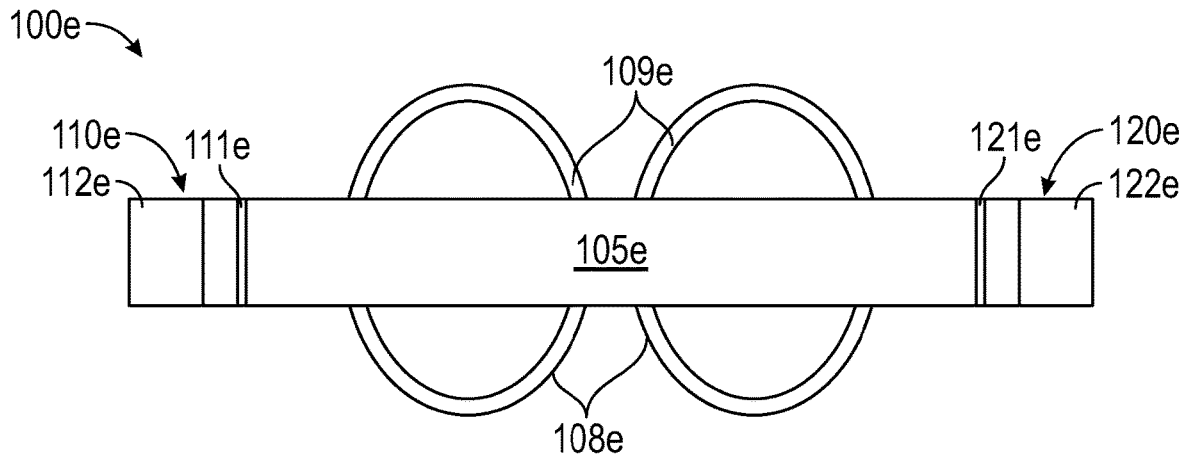
Figure 6C:
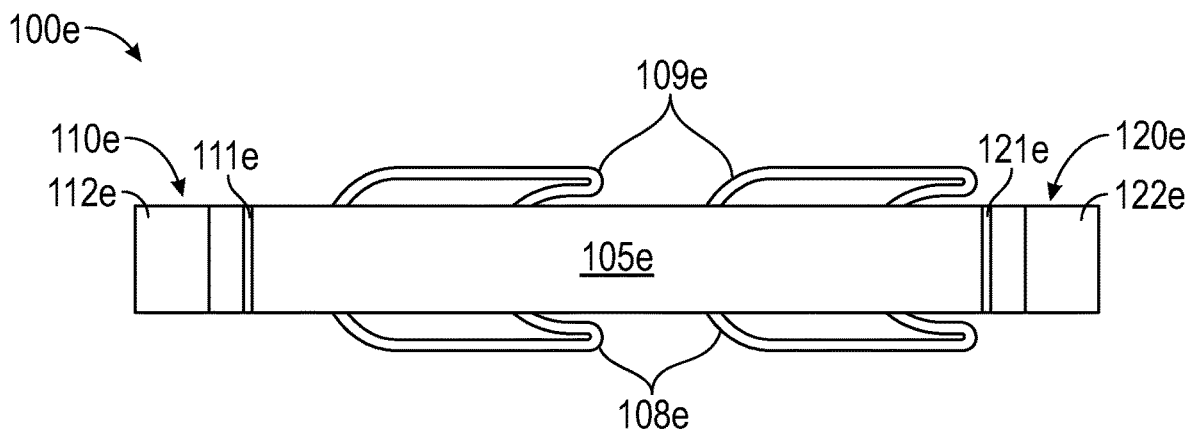
FIG. 6C is a top view of the delivery tool depicted in FIGS. 6A-6B in a generally unidirectional configuration as described in at least one embodiment herein.

In FIGS. 6A-6C, the multi-directional magnetic delivery tool 100e includes first and second magnetic members 112e, 122e, first and second loop tie slots 111e, 121e, positioned on first and second distal end portions 110e, 120e, with elongate body 105e extending therebetween and further including resilient arms 108e extending from the elongate body 105e at two or more locations. Unlike the pivotable arm 109d in FIGS. 5A and 5B, the resilient arms 108e do not rotate about the elongate body 105e. Rather, the resilient arms 108e are generally designed to maintain the extended configuration shown in FIG. 6A whenever unrestrained. As depicted in FIG. 6C, in order to be received within the rolling device and/or pass through a trocar, the resilient arms 108e can be deformed, i.e., bent, folded, pressed, against the elongated body 105e to form a generally unidirectional configuration and to a size sufficiently small enough to fit and pass through the rolling device and/or the trocar. In addition, upon insertion into the patient, the resilient arms 108e are released from the restraints of the rolled implantable sheet, the rolling device, and/or the trocar walls to naturally return to their original expanded configuration (FIGS. 6A-6B). In some embodiments, the resilient arms form rounded or elliptical arms affixed to and extending from at least two different locations on the elongate body.

The resilient arms can be made from any suitable material. Some non-limiting examples of suitable resilient materials include nitinol, polycarbonate, polyethylene terephthalate, polyurethane, polyamides, polyether ether ketones, high-density polyethylene, polyethylene, Some non-limiting examples of suitable materials include polyethylene, polypropylene, polyamides, polyaryl ether ketone (PAEK), acrylonitrile butadiene styrene (ABS), polyether ether ketone (PEEK), polyoxymethylene (POM), polyetherimide (PEI), polycarbonates (PC), and combinations thereof. In some embodiments, at least the resilient arms of the delivery tool insert can be made from polyamides, polyether ether ketone (PEEK), and nitinol (NiTi).

Figure 7D:
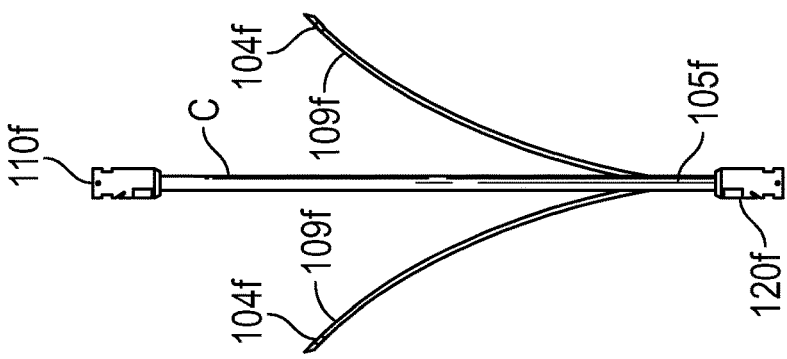
FIGS. 7B-7D are top views of the delivery tool depicted in FIG. 7A in various multidirectional configurations as described in at least one embodiment herein.
Figure 7C:
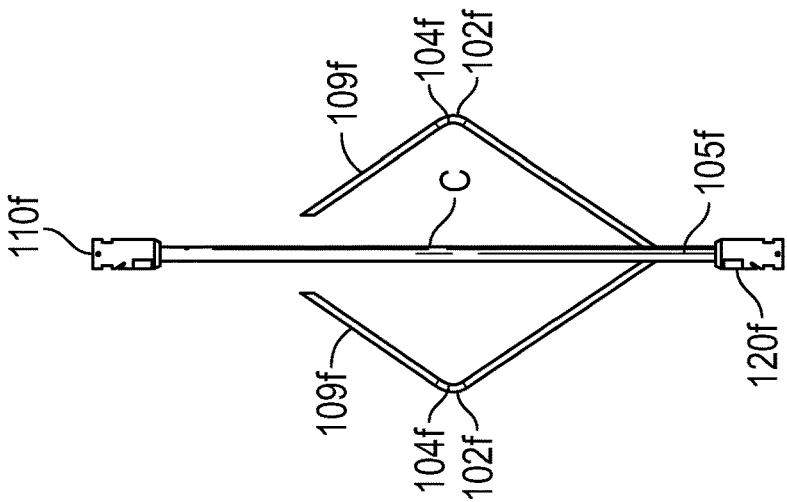
Figure 7B:
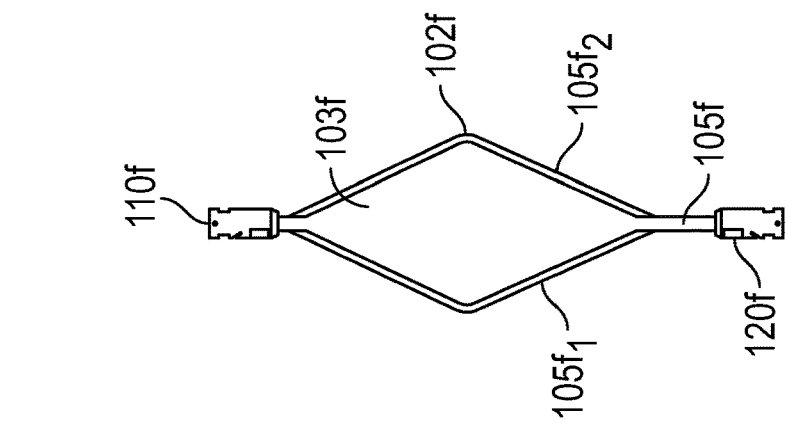
Figure 7A:
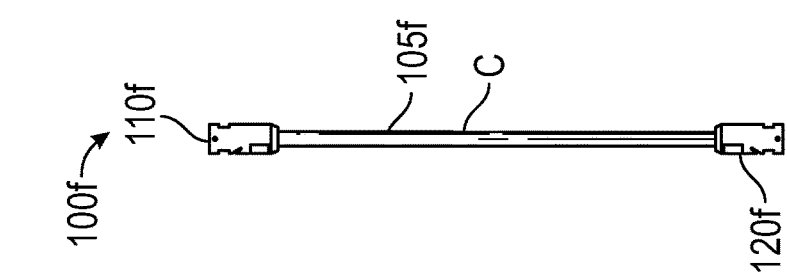
FIG. 7A includes a top view of a delivery tool in a unidirectional configuration as described in at least one embodiment herein.

In FIGS. 7A-7D, the multidirectional delivery tools 100f includes proximal and distal end portions 110f, 120f as described herein (including first and second magnetic members and first and second loop tie slots therein) with elongate body 105f extending therebetween, the elongate body 105f further configured to transition between an unidirectional configuration (FIG. 7A) and a multidirectional expanded configuration (FIGS. 7B-7D). In FIG. 7B, the elongate body 105f includes a slice 103f running a length of the elongate body 105f splitting the elongate body 105f into two pivotable parts $105f_1$, $105f_2$. The two pivotable parts $105f_1$, $105f_2$ connected to each other near or at the proximal and distal end portions 110f, 120f. Each pivotable part $105f_1$, $105f_2$ of the elongate body 105f includes a joint 102f designed to bend away from the slice 103f, and each other, thereby expanding the opening of the slice 103f. When straightened, the pivotable parts $105f_1$, $105f_2$ abut against each other to close the slice 103f to form the unidirectional configuration.

In some embodiments, the pivotable parts $105f_1$, $105f_2$ of the elongate body $105f$ can be separated from each other manually by the surgeon, either directly or with the assistance of a surgical robot, inside the patient's body. In some embodiments, the pivotable parts $105f_1$, $105f_2$ of the elongate body $105f$ maintain and display a natural bias to pivot away from each other. In such embodiments, the rolling device and/or the rolled implantable sheet may be used, prior to insertion, to prevent the naturally biased pivotable parts $105f_1$, $105f_2$ from pivoting away from each other prematurely.

In FIGS. 7C-7D, the elongate body $105f$ includes a plurality of curved or bent arms $109f$ which are configured to expand away from the elongate body $105f$. In some embodiments, each of the curved or bent arms $109f$ further include at least one arm magnetic member $104f$ configured to be engaged with the magnetic members of the positioner to be rotated or pivoted away from the elongate body $105f$. As shown specifically in FIG. 7C, in some embodiments, the at least one arm magnetic member $104f$ is positioned on or near the joint $102f$. As shown specifically in FIG. 7D, in some embodiments, the at least one arm magnetic member $104f$ is positioned on or near an end portion of the arm $109f$.

In some embodiments, the delivery tool is a unidirectional delivery tool and the implantable sheet is a surgical mesh. In some embodiments, the delivery tool is a multidirectional delivery tool and the implantable sheet is a surgical mesh.

IV. Positioner

The positioners described herein are configured to magnetically engage the magnetic member(s) of the delivery tools from outside the patient's body. The positioner, unlike the delivery tool, is not intended to enter inside a patient.

Figure 8:
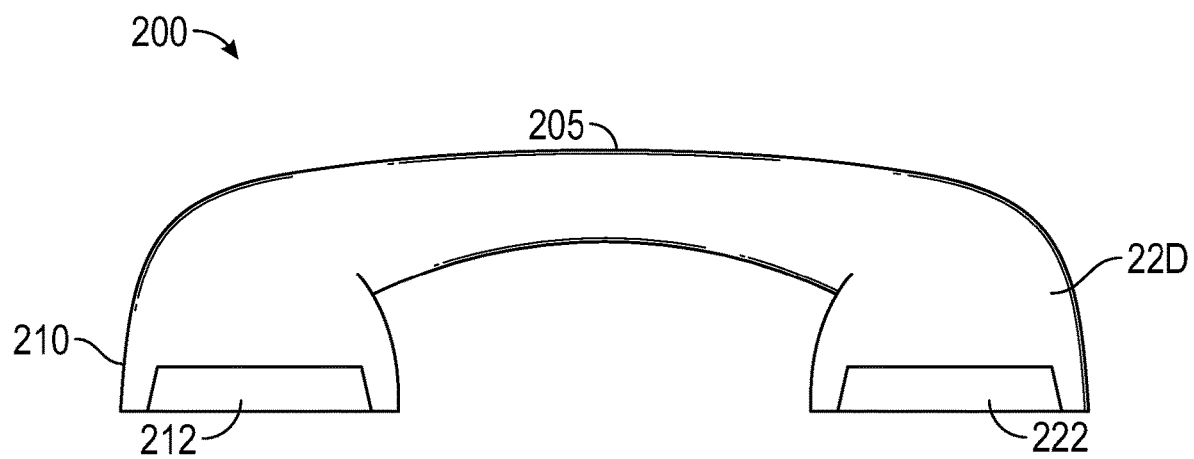
FIG. 8 includes a side view of a positioner described in at least one embodiment herein.

As depicted in FIG. 8, the positioner 200 includes a handle 205 extending between a proximal end portion 210 and a distal end portion 220 of the positioner 200. The proximal end portion 210 includes a first magnetic member 212 and the distal end portion 220 includes a second magnetic member 222.

The first and second magnetic members of the positioner are complimentary to the first and second magnetic members of the delivery tool. By complimentary, the magnetic members of the positioner magnetically attract or are magnetically attracted to the magnetic members of the delivery tool and vice-versa to allow the magnetic members of the positioner and the magnetic members of the delivery tool to magnetically engage each other.

As further shown, in some embodiments, the handle 205 may extend between the proximal and distal end portions 210, 220 in a manner which creates an arc between the proximal and distal end portion 210, 220. In some embodiments, the handle 205 is rounded. In some embodiments, as further depicted in FIG. 8, the proximal and distal end portions 210, 220 are generally round members. In some embodiments, the positioner may generally define the shape of a telephone receiver.

As further depicted in FIG. 8, the handle 205 is positioned at the top of each of the proximal and distal end portions 210, 220 thereby spacing the handle 205 from the outer surface of the patient's skin when utilized. This spacing allows a surgeon, either directly or with the assistance of a surgical robot, to grab the handle without touching the patient's outer skin and rotate the positioner without interfering or losing the magnetic engagement between the positioner and the delivery tool.

Figure 9:
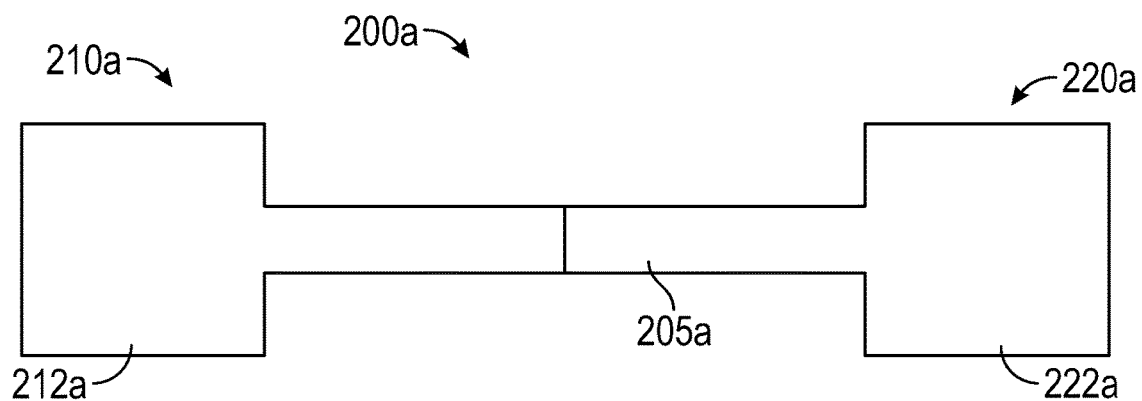
FIG. 9 includes a side view of a positioner described in at least one embodiment herein.

In FIG. 9, the positioner 200a includes proximal and distal end portions 210a, 220a having a polygonal and/or rectangular configuration wherein the straight handle 205a extends from a central portion of the proximal and distal end portions 210a, 220a without forming an arc therebetween while still remaining spaced from the base of the positioner 200a for easy manipulation of the positioner. In some embodiments, the positioner may be of one-piece construction. In some embodiments, the positioner may be made from two or more pieces.

In some embodiments, a portion of the proximal and distal end portions are made from a magnetic material or magnet to form the magnetic member. In some embodiments, the magnetic members are covered by any biocompatible material, and particularly a biocompatible material which is magnetically inert or does not negatively affect the strength of the magnetic force between the positioner and the delivery tool. Some non-limiting examples of suitable materials include polyethylene, polypropylene, polyamides, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), silicone, stainless steel, iron, and combinations thereof.

V. Rolling Device

The rolling devices described herein are configured to prepare the implantable sheet and the delivery tool for insertion into a patient. The rolling device is used to wrap the implantable sheet around an outer surface of the flexible delivery tool to render the sheet in a rolled configuration prior to insertion into a patient. The rolling device may also be used by a surgeon to transfer the delivery tool including the implantable sheet in a rolled configuration to a trocar for insertion into a patient. The rolling device, unlike the implantable sheet and delivery tool, is not intended to be inserted into a patient.

Figure 10A:
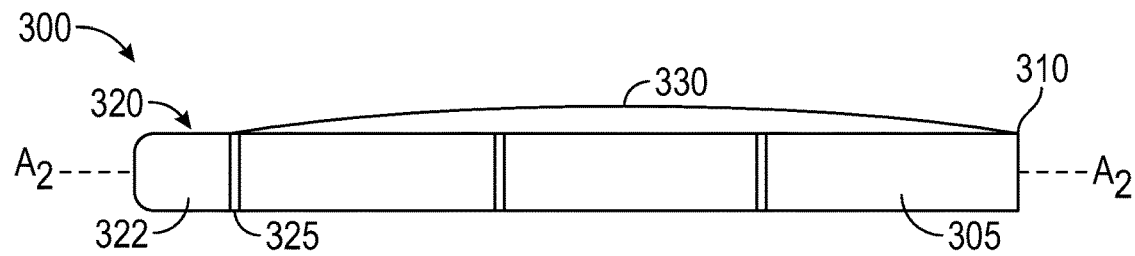
FIGS. 10A-10B include a side view, and an end view, respectively, of a rolling device described in at least one embodiment herein.
Figure 10B:
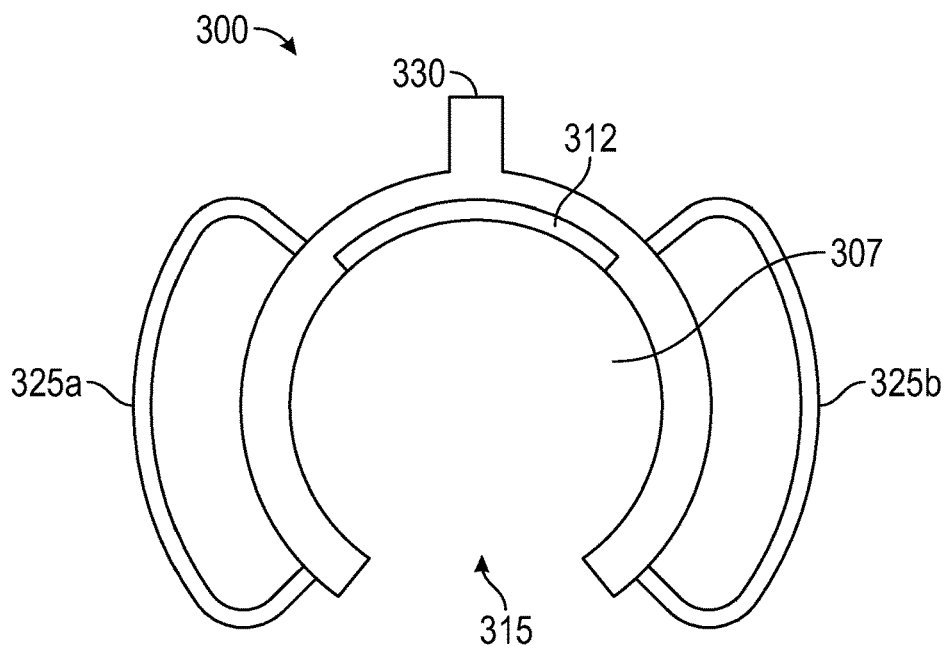

In FIGS. 10A-10B, a rolling device 300 is shown including a generally tubular body 305 extending between a proximal end portion 310 and a distal end portion 320 of the device 300, the tubular body 305 generally defines a channel 307 configured to receive both the implantable sheet and the delivery tool. The channel 307 extends the entire length of the tubular body 305 through both the proximal and distal end portions 310, 320 of the device 300. A first slit 315 also extends the entire length of the tubular body creating an open generally tubular body 305 and/or an open channel 307. At least one fin 330 also extends along a length of the tubular body 305 and on an outer surface of the tubular body 305. In some embodiments, the rolling devices described herein may further include at least one magnetic member 312 positioned on an inner surface the tubular body 305. The magnetic member 312 being configured to assist with drawing the proximal and distal end portions of the delivery tool into the channel 307 through the first slit 315 by attracting a magnetic member(s) of the delivery tool.

The first slit 315 is configured to allow passage of the implantable sheet and delivery tool into the channel 307 of the tubular body 305. The first slit 315 also provides the rolling device 300, which can be made of a rigid or semi-rigid material, the flexibility to expand or contract along the slit 315 as needed to accommodate different size implantable sheets and/or delivery tools.

The rolling device 300 further includes a spout 322 and at least one flange 325 extending from the distal end portion 320. The spout 322 extends from the distal end portion 320 along the longitudinal axis $A_4$ of the device 300 and is configured to fit within or mate with a trocar opening to allow access into the trocar during insertion or retrieval of the implantable sheet and/or delivery tool. The at least one flange 325 is positioned on the distal end portion 320 proximal to the spout 322 and extends generally perpendicular to longitudinal axis $A_4$ of the device 300. In some embodiments, the device 300 may include two flanges 325a, 325b, each positioned on opposite sides of the device 300. In some embodiments, the spout 322 can be designed as two separate half-circles, each positioned on opposite sides of the first slit 315.

Figure 11:
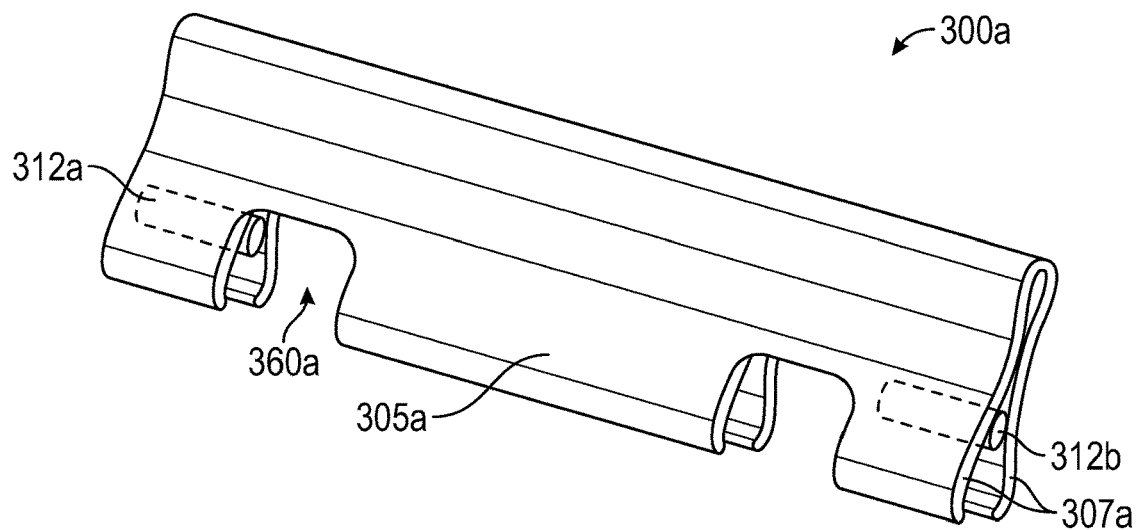
FIG. 11 is a perspective view of a rolling device described in at least one embodiment herein.

As depicted in FIG. 11, in some embodiments, the elongate body 305a, the channel 307a and/or the first slit 315a, of a rolling device 300a, may be discontinuous and do not extend completely across the entire length of the device creating open spaces 360a between portions of the elongate body 305a. Also, in some embodiments, the rolling device 300a may not include a spout or flange extending from a distal end portion thereof.

In still other embodiments, as further shown in FIG. 11, the rolling device 300a described herein may further include at least one magnetic member 312a, 312b positioned on an inner surface the tubular body 305a on the proximal and/or distal end portion(s) 310a, 320a of the rolling device 320. In some embodiments, the rolling devices described herein do not include a magnetic member.

The rolling device can be made of any suitable material. Some non-limiting examples of suitable materials include stainless steel, polyethylene, polypropylene, polyamides, polyurethanes, polyethylene terephthalate, polyethylene terephthalate glycol modified, polyethylene high density, polyethylene low density, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof.

In addition to the various rolling devices described hereinabove, in some embodiments, the rolling device is a rolling device described in any of U.S. Pat. Nos. 8,317,808; 8,734,473; 9,364,311; 10,052,126; and 10,016,265, each of which are incorporated herein by reference.

VI. Insertion Member

The insertion members described herein are configured to connect or attach to the proximal end of the delivery tool. Once attached, the insertion members are designed to rotate the delivery tool causing the implantable sheet to wrap around the exterior of the delivery tool into a rolled configuration. Therefore, the insertion member provides a dual ability or function for both rolling and inserting of the implantable sheet and delivery tool.

Figure 12A:
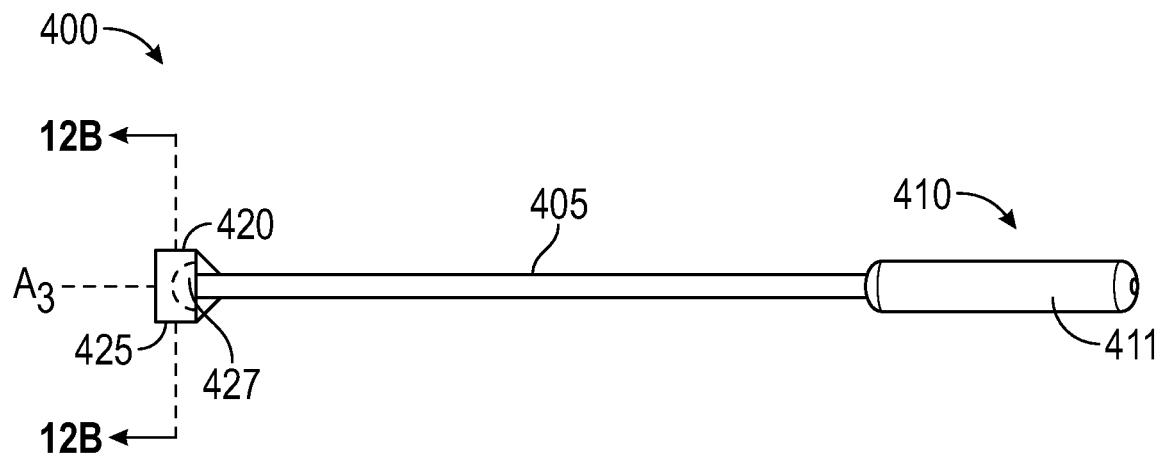
FIGS. 12A-12B include a side view and an end view, respectively, of an insertion member described in at least one embodiment herein.

FIG. 12A depicts an insertion member 400 having an elongate body 405 extending between a proximal end portion 410 and distal end portion 420 of the insertion member 400. The proximal end portion 410 of the insertion member 400 includes a handle or grip 411 designed to assist with moving the insertion member 400 longitudinally through the trocar and also with rotating of the insertion member 400 which in turn rotates the delivery tool inside the rolling device. The distal end portion 420 of the insertion member may include a socket 425 designed to mate with the proximal end portion of the delivery tool. The socket 425 including a socket cavity 426 having an inner perimeter which matches the outer perimeter of the shaped proximal end portion of the delivery tool, so the shaped proximal end portion of the delivery tool can be received within the socket cavity 426. The socket cavity 426 may also include a socket protrusion 427 positioned within the cavity 426 which mates and/or properly sits within the indentation of the delivery tool. When attached, the insertion member 400 and the delivery tool share a common central longitudinal axis $A_3$. The insertion member 400 has a length that is longer than a typical trocar used for laparoscopic surgery. In some instances, the insertion member has a length that is longer than a trocar and a rolling device as described herein combined.

Figure 12B:
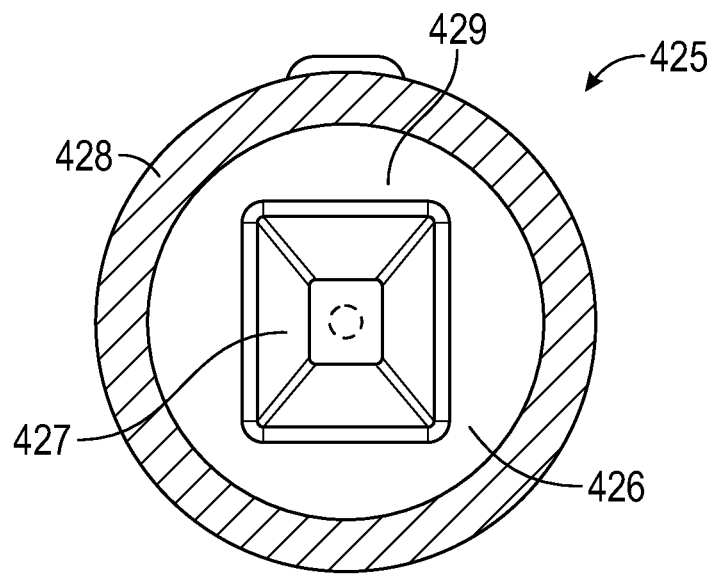

FIG. 12B shows an end view into the socket on the distal end portion 420 of an insertion member 400 along the longitudinal axis $A_3$. The socket 425 shown is configured to matingly engage with the circular shaped proximal end of FIG. 3B. The socket 425 includes a socket cavity 426 having a shape or contour which mirrors the shaped proximal end portion 210a of a delivery tool 200a. The socket cavity 426 including at least one sidewall 428 and a base 429 which together define the cavity 426. As shown, in some embodiments, the base 429 may further include a socket protrusion 427 configured to matingly engage an indentation carved into a proximal end of a delivery tool. The projection also having a shape or contour which mirrors the shape or contour of the indentation to ensure proper mating.

In some embodiments, the insertion member further includes an articulation means or articulation joint positioned along the elongate body between the socket and the handle. In some instances, the articulation means or articulation joint is positioned nearest the socket to best facilitate the separation of the insertion member from the flexible delivery tool by limiting a long over-center locking by the socket. In some embodiments, the articulation joint may allow passive articulation via a ball and socket joint which could locked by a locking collar slid over the joint thereby locking the member into a straight configuration, and when slid off the joint allowing the locking member to articulate.

The insertion member can be made of any suitable material. Some non-limiting examples of suitable materials include stainless steel, polyethylene, polypropylene, polyamides, polyurethanes, polyethylene terephthalate, polyethylene terephthalate glycol modified, polyethylene high density, polyethylene low density, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof.

VII. Sheet-Tool Assembly

Figure 13B:
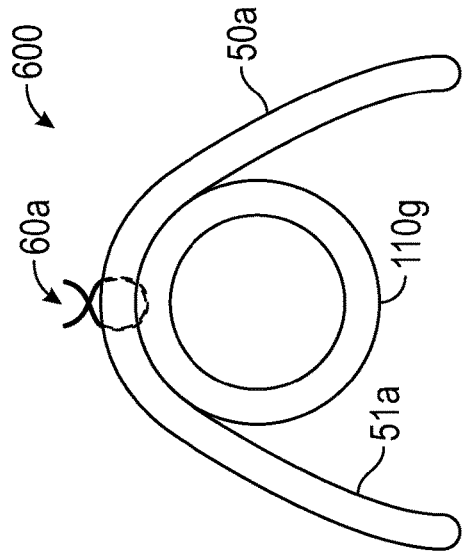
FIGS. 13A-13C include a top view, end view, and side view, respectively, of a sheet-tool assembly described in at least one embodiment herein.
Figure 13A:
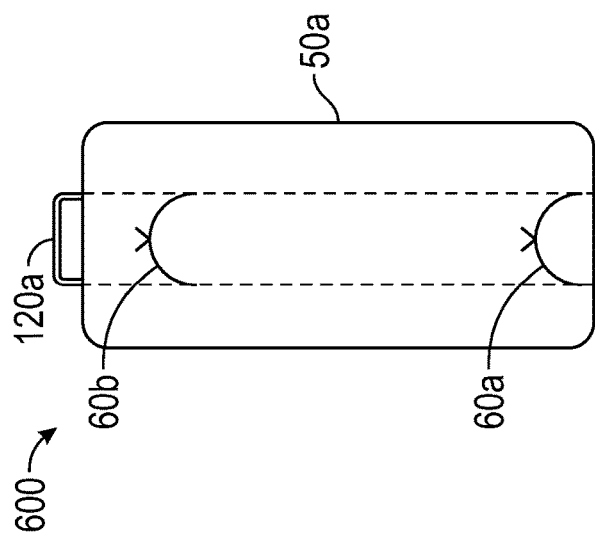
Figure 13C:
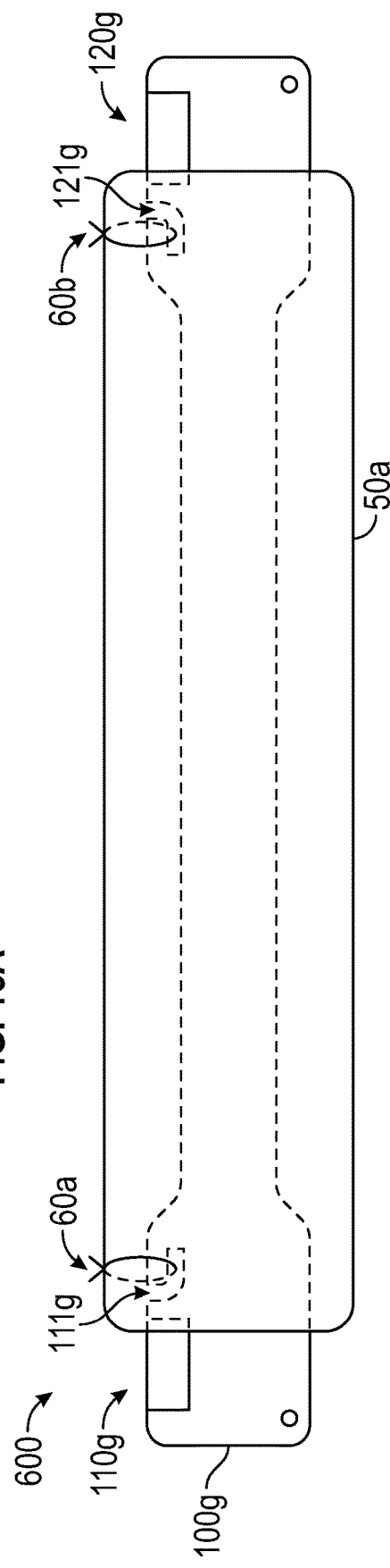

In FIG. 13A-13C, a sheet-tool assembly 600 is depicted wherein the implantable sheet 50a is shown secured to the delivery tool 100g by a first and second loop tie 60a, 60b extending from a bottom side 51a of the sheet 50a and is positioned and secured within the first and second loop tie slots 111g, 121g thereby securing the sheet 50a to the proximal and distal end portions 110g, 120g of the delivery tool 100g to form the sheet-tool assembly 600.

The sheet-tool assembly may be preassembled prior to packaging or may be post-assembled after the package is opened and the components accessed.

Pre-assembly of the implantable sheet with the delivery tool and the one or more loop ties provides the benefit of decreasing the length of time needed to perform the surgical procedure. Pre-assembly is also the easiest way for the medical personnel to handle the implantable sheet and delivery tool prior to implantation. However, pre-assembly can also add stress to the implantable sheet, via the delivery tool, during storage or transportation which can lead to damage of the implantable sheet, especially when the sheet includes a coating or the sheet is a composite mesh including additional layers such as an anti-adhesion barrier. Coatings and anti-adhesion barriers can be fragile and could suffer damage, such as cracks, scratches, chipping, etc. by rubbing against the delivery tool during shipment or storage.

In some embodiments, the implantable sheet is an implantable mesh and the sheet-tool assembly is a mesh-tool assembly.

VIII. Methods of Use

The present disclosure also provides methods of treating or repairing soft tissue defects with the use of the various components of the kits described herein. The kits and components described herein are intended to be used in any variety of surgical procedures wherein a soft tissue defect needs repair. In some embodiments, the kits and components described herein may be used to repair various types of hernia repair including but not limited to ventral hernia repair. In some embodiments, the kits and components described herein may be used in TAPPS, TEPS, or IPOM surgical techniques. Any methods described herein directed to repairing a soft tissue defect or hernia is intended to be applicable specifically to ventral hernia repair and/or ventral hernia using an IPOM surgical technique.

As provided in FIG. 14A-15E, methods for repairing a soft tissue defect, such as a ventral hernia, may include the steps of preparing a sheet-tool assembly, preparing the sheet-tool assembly for insertion into the patient, inserting the sheet-tool assembly into the patient, positioning, deploying, and fixating the sheet, detaching the implantable sheet from the delivery tool and the one or more loop ties, and removing the delivery tool from a body cavity of the patient.

Prior to using the components and/or kits described herein to treat or repair a soft tissue defect, at least some of the components may be combined or assembled. For example, in some embodiments, the implantable sheet, the one or more loop ties, and the delivery tool may be assembled to form a sheet-tool assembly, wherein the one or more loop ties, the delivery tool, and the implantable sheet are combined in one or more additional procedural steps. For example, in some embodiments, a method of forming a sheet-tool assembly is described and includes the steps of: providing an implantable sheet having an outer edge defining a central longitudinal axis of the sheet; adding one or more loop ties along the central longitudinal axis of the implantable sheet, particularly on a proximal and distal end portion of the sheet, such that the one or more loop ties form a loop extending from a bottom side of the sheet and configured to be received within a loop tie slot defined within a delivery tool; and positioning the loop of the one or more loop ties into a loop tie slot defined within a delivery tool thereby forming a sheet-tool assembly, and specifically, securing the bottom side of the sheet to the top side of the delivery tool.

Figure 14A:
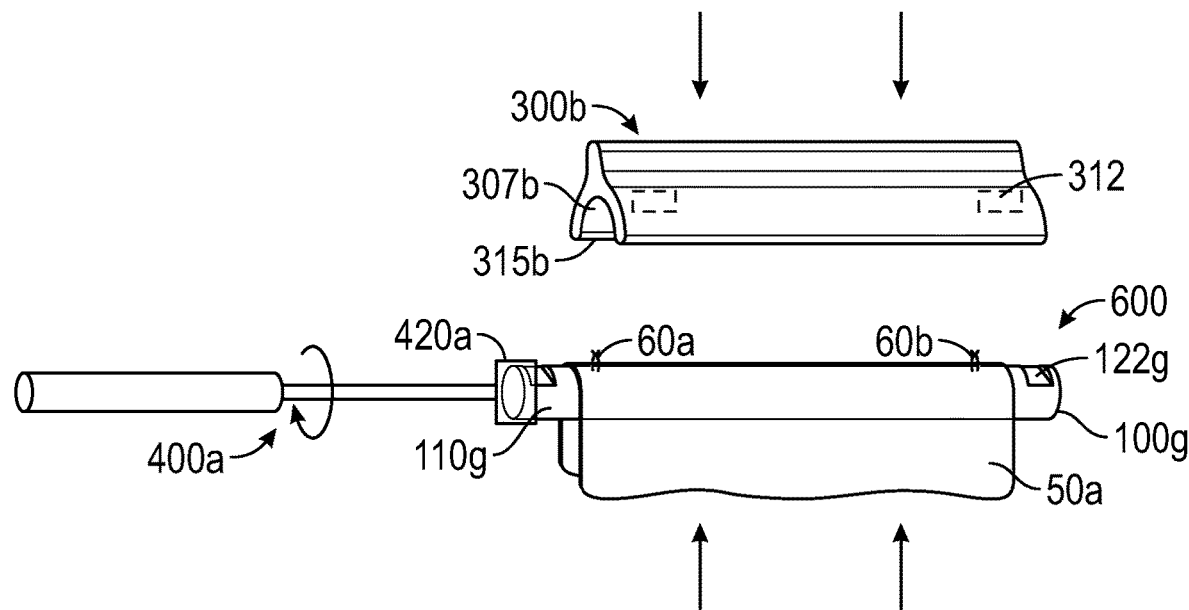
FIGS. 14A-14B are perspective views of a rolled sheet-tool assembly described in at least one embodiment herein.
Figure 14B:
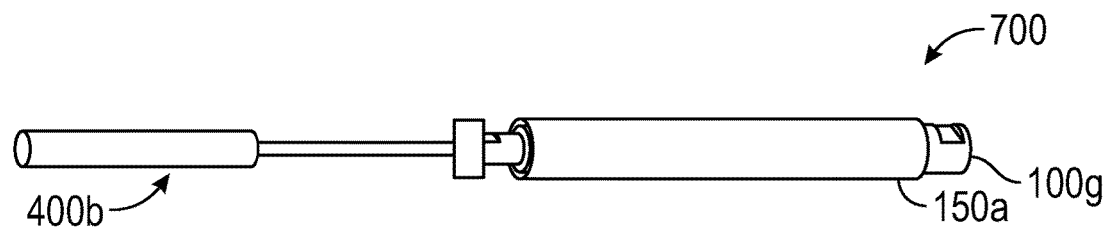
Figure 15A:
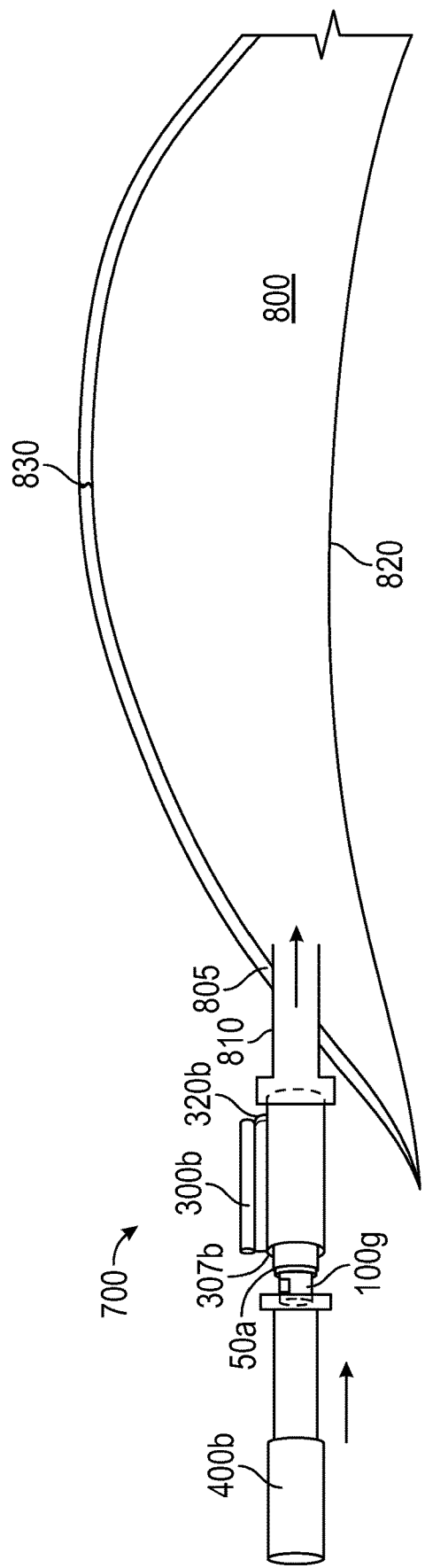
FIGS. 15A-15E are cross-sectional schematic views of a method of using the kits and/or components described herein in treating a soft tissue defect as described in at least one embodiment herein.

Once assembled, the implantable sheet, the loop tie(es), and the delivery tool, i.e., the sheet-tool assembly, can be prepared for insertion into the patient. For example, as shown in FIGS. 14A-14B, in some embodiments, the sheet-tool assembly 600, whether pre-assembled within the package or post-assembled after the package is opened, can be combined with a rolling device 300b and a insertion member 400a to roll the implantable sheet 50a around the exterior of the delivery tool 100g in one or more additional procedural steps. In some embodiments, a method of preparing a rolled sheet-tool assembly for insertion into a patient is described and includes the steps of: connecting a distal end portion 420a of the insertion member 400a to a proximal end portion 110g of a delivery tool 100g, the delivery tool 100g secured to an implantable sheet 50a via one or more loop ties 60a, 60b forming the sheet-tool assembly; passing the sheet-tool assembly 600 through slit 315b of the rolling device 300b to position the sheet-tool assembly within channel 307b of the rolling device 300b; and rotating the insertion member 400a (as indicated by the arrow) with the sheet-tool assembly positioned within the channel 307b causing the implantable sheet 50a to roll onto itself around the outer surface of the delivery tool 100g to form a rolled implantable sheet or a rolled sheet-tool assembly 700. In some embodiments, as shown in FIG. 14B, the rolling device 300b may be removed from the rolled sheet-tool assembly 700 prior to insertion of the rolled sheet-tool assembly into a patient. In some embodiments, as shown in FIG. 15A, the rolled sheet-tool assembly 700 may be transported to a patient while remaining positioned within the channel 307b of the rolling device 300b and connected to the insertion member 400b.

In some embodiments, the implantable sheet is an implantable mesh and the rolled sheet-tool assembly is a rolled mesh-tool assembly.

In some embodiments, a distal end portion of an insertion member, and particularly a socket on the distal end portion of the insertion member, can be secured to the shaped proximal end of the delivery tool prior to rolling. In such embodiments, the step of rotating the delivery tool can be performed by rotating the insertion member attached thereto. By using the insertion member, human contact to the proximal end of the delivery tool is avoided to reduce the likelihood of contamination.

Figure 15B:
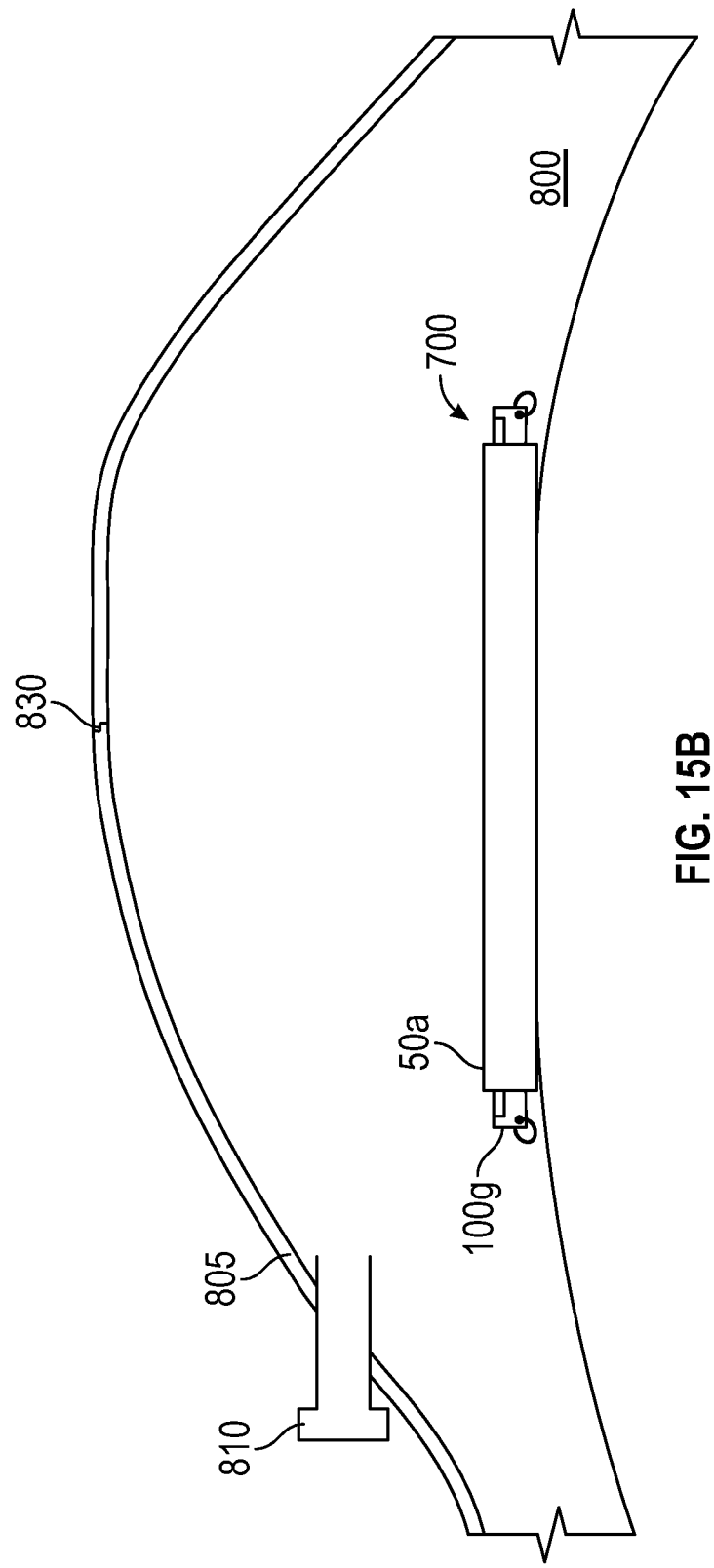

Once the implantable sheet is prepared in a rolled configuration or the rolled sheet-tool assembly is prepared, the rolled sheet or rolled sheet-tool assembly can be inserted into an abdominal cavity of a patient. For example, as shown in FIGS. 15A-15B, in some embodiments, a method of inserting a rolled sheet or rolled sheet-tool assembly is described and includes the steps of: attaching a distal end portion 320b of the rolling device 300b to a trocar 810 extending from the patient's body 805, such as the abdominal cavity 800; and moving or pushing the insertion member 400b in a distal direction (see arrows) through the channel 307b of the rolling device 300b and into the trocar 810 until the delivery tool 400b including the implantable sheet 50a in a rolled configuration or the rolled sheet-tool assembly 700 completely enters a cavity 800 within the patient, such as the abdominal cavity 800. In some embodiments, the rolling device 300b and the insertion member 400b can be used as handles during the insertion process to carry the rolled sheet 50a and tool 100g from the package 500 to the trocar 810. A surgeon, either directly or with the assistance of a surgical robot, can easily grab the rolling device 300b on one end and the insertion member 400b on an opposite end, with the implantable sheet 50a and delivery tool 100g positioned therebetween in a rolled configuration (or rolled sheet-tool assembly 700), to perform inserting the sheet 50a and delivery tool 100g into the patient. Since the rolling device and the insertion member are not intended to enter the patient, human contact does not need to be avoided to prevent contamination. This design also prevents or limits the amount of direct contact with the implantable sheet and the delivery tool thereby further reducing the likelihood of contamination.

Figure 15C:
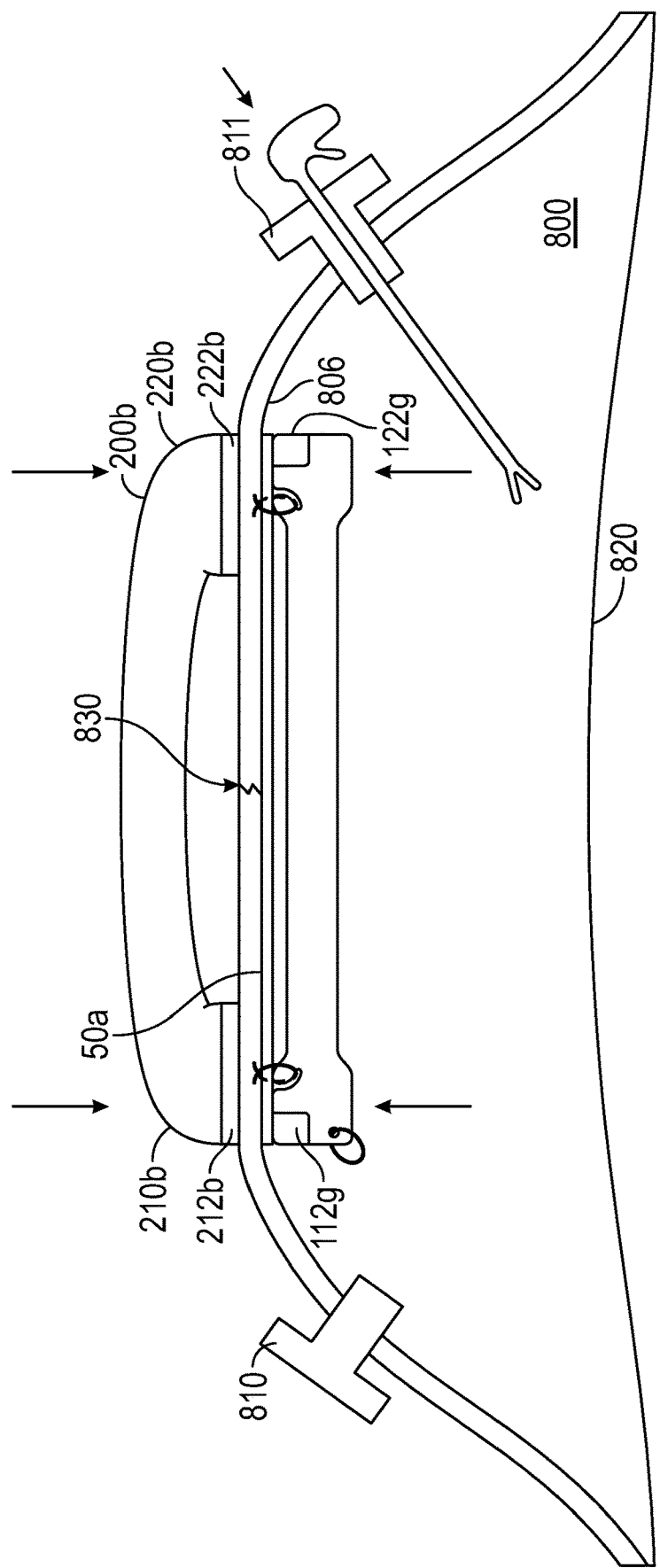

Once the rolled sheet-tool assembly is inserted into a cavity of a patient, the implantable sheet can be positioned, unrolled or deployed, and/or fixated to the patient's tissue. For example, as shown in FIG. 15C, in some embodiments, a method of positioning, deploying, and fixating the rolled implantable sheet or rolled sheet-tool assembly is described and includes the steps of: placing a magnetic positioner 200b onto an outer surface of the patient's body 805 directly above the cavity 800 to draw the first and second magnetic members 112g, 122g of a delivery tool 100g to the first and second magnetic members 212b, 222b, of the magnetic positioner 200*b* thereby lifting the rolled-sheet tool assembly 700 from the base 820 of the body cavity 800 to a top 806 of the body cavity 800 and up against the inside of tissue defect 830; deploying the sheet 50*a* of the rolled sheet-tool assembly 700 to cover the tissue defect or hernia 830; and fixating the deployed sheet 50*a* to the tissue surrounding the tissue defect 830. The magnetic positioner remains in contact with the outer surface of the patient's body 805 while the steps of positioning, deploying, and/or fixating of the sheet 50*a* are performed. The delivery tool 100*g* remains secured to the sheet 50*a* via loop ties 60*a*, 60*b* while the steps of positioning, deploying, and/or fixating of the implantable sheet 50*a* are performed.

As further depicted in FIG. 15C, in some embodiments, the positioner 200*b* may be properly positioned when the proximal and distal end portions 210*b*, 220*b* of the positioner 200*b* are located on opposite sides of the tissue defect 830. When in position, an attractive magnetic force is created which draws the first and second magnetic members 111*g*, 121*g* of the delivery tool 100*g* upwards (as indicted by the arrows) from the base 820 of the body cavity 800 towards the first and second magnetic members 212*b*, 222*b* of the positioner 200*b* thereby forming magnetic engagement between the delivery tool 100*g* positioned inside the body cavity 800 and the positioner 200*b* positioned outside the body cavity 800. The positioner 200*b* and the delivery tool 100*g* are held together magnetically with the implantable sheet 50*a* positioned therebetween beneath the tissue defect 830.

As further provided in FIG. 15C, at least one additional surgical tool 811, such as a surgical grasper or surgical fastener, may be passed through a second or more trocars 810 and into the cavity 800 to assist with positioning, deploying, and/or fixating of the sheet 50*a*.

Any standard laparoscopic surgical tool, grasper or standard surgical fastening device, such as a tack or clip applier, stapler, or suturing device, may be introduced into the patient via one or more trocars. Because the implantable sheet remains sandwiched between the delivery tool on one side and the positioner and the tissue on the opposite side, due to the magnetic engagement between the delivery tool and the positioner, both hands of the surgeon are free to work in unison to deploy, position and/or fixate the implantable sheet to the tissue. The sheet can be fixated using any suitable fixation means, including, but not intended to be limited to, sutures, clips, tacks, staples, adhesives, and the like.

Figure 15D:
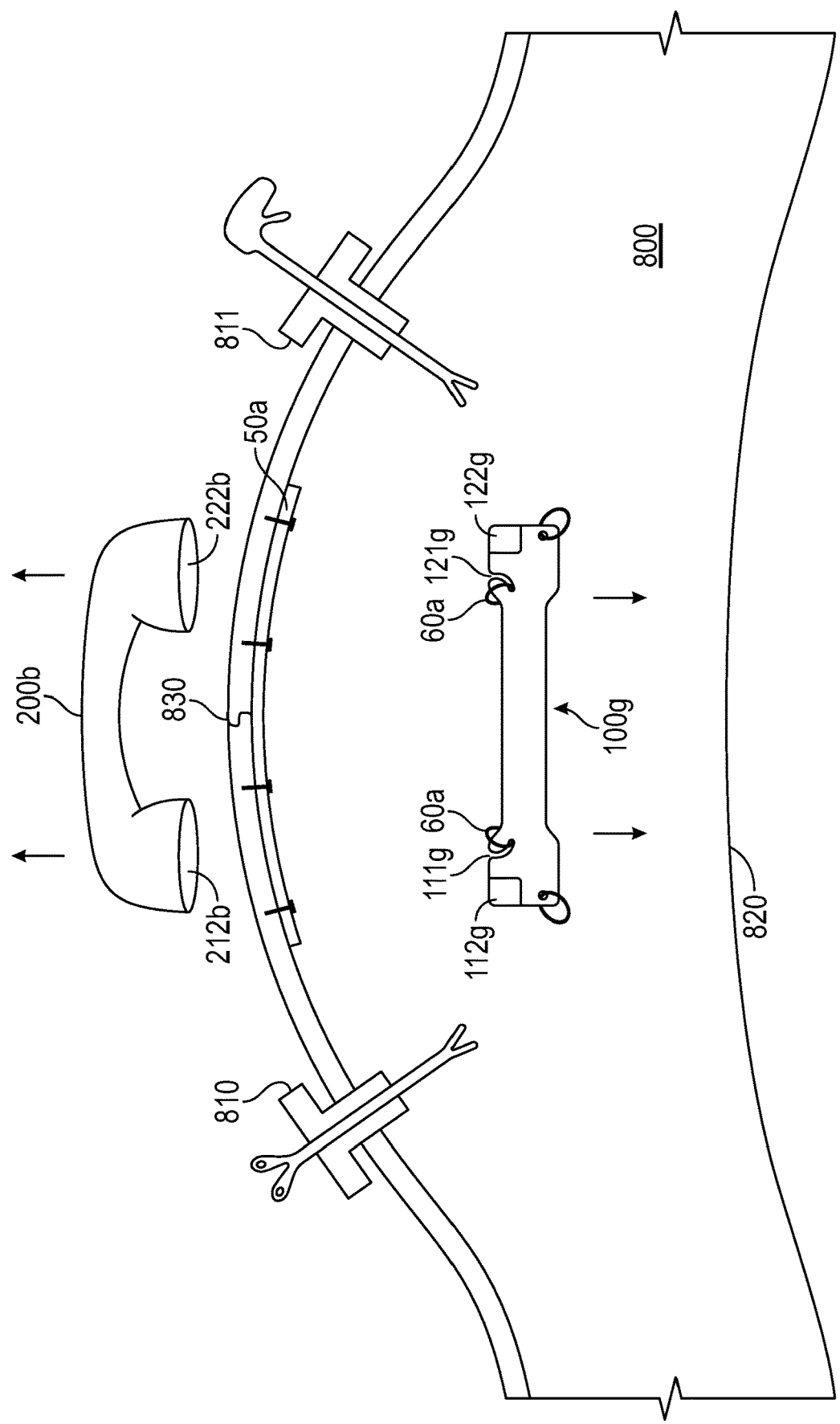
Figure 15E:
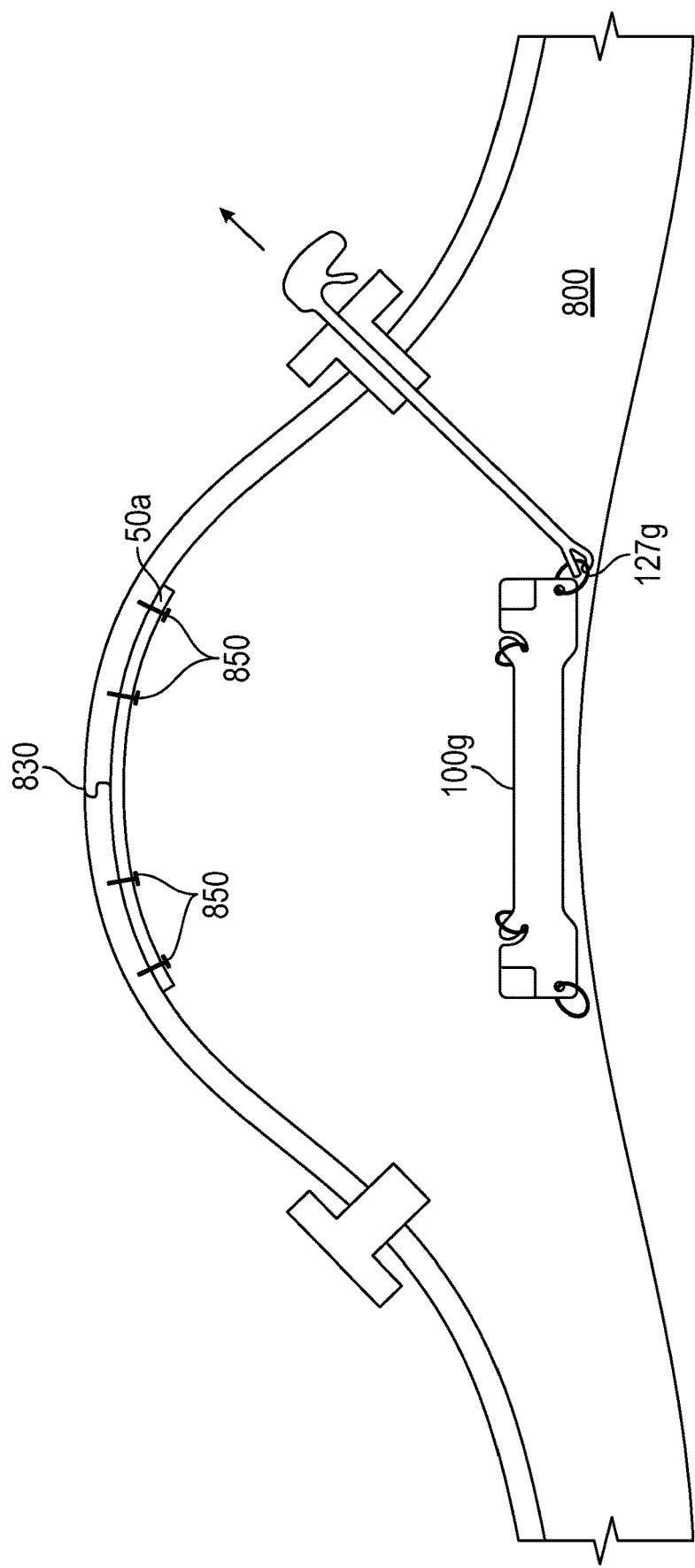

Following positioning, deployment, and/or fixation of the implantable sheet, the positioner can be separated from the delivery tool, the delivery tool and the one or more loop ties can be separated from the sheet, and the delivery tool can be withdrawn from the patient's body. For example, as shown in FIGS. 15D-15E, in some embodiments, a method of withdrawing a delivery tool 100*g*, with or without the loop tie(es) 60*a*, from the patient is described and includes the steps of: removing a magnetic positioner 200*b* from an outer surface of the patient's body 805 to disengage the magnetic engagement between the magnetic positioner 200*b* (and specifically the magnetic members 212*b*, 222*b* of the positioner 200*b*) and the delivery tool 100*g* (and specifically the magnetic members 112*g*, 122*g* of the delivery tool 100*g*); removing the one or more loop ties 60*a* from the sheet 50*a* and/or the loop tie slot 111*g*, 121*g* thereby freeing the sheet 50*a* from the delivery tool 100*g*; and withdrawing the delivery tool 100*g* and loop tie(es) 60*a* from inside the patient. Following the removal of the magnetic positioner from the outer surface of the patient's body, the delivery tool 100*g* remains at the top of the cavity 800 because the delivery tool 100*g* is still secured to the sheet 50*a* by the loop ties 60*a* and the sheet 50*a* is secured to the tissue by the fastening elements 850. Removal of the loop ties 60*a* can occur by simply cutting the stitches 60*a* thereby eliminating the loop in the loop tie. In addition, or in the alternative, the surgeon, either directly or with the assistance of a surgical robot, may use one of the surgical tools to grab the delivery tool 100*g* to slide the delivery tool 100*g* longitudinally along an outer surface of the sheet 50*a* until the loop tie 60*a* (or any partial remnant thereof after cutting) is backed out of the loop tie slot 111*g*, 121*g*.

In some embodiments, the loop tie slots of the delivery tool may extend in the same direction (as shown in FIG. 4A) and therefore may be able to be removed by sliding the delivery tool in only one longitudinal direction. In some embodiments, wherein the loop tie slots of the delivery tool extend away from each in opposite directions (as shown in FIGS. 2A and 3A) and therefore may need to be slid longitudinally in two directions, i.e., a back and forth direction or proximal then distal direction, to sequentially free the first loop tie from the first loop tie slot and then the second loop tie from the second loop tie slot.

Once the delivery tool 100*g* is free of the implantable sheet 50*a*, the delivery tool 100*g* falls back to the base 820 of the cavity 800 to await withdrawal from the patient. The surgical tool or grasper can be used to grab the distal end portion 120*g* of the delivery tool 100*g*, and particularly the suture loop 127*g* positioned through the suture aperture 126*g* on the distal end portion 120*g* of the delivery tool 100*g*, to withdraw the distal end portion 120*g* of delivery tool 100*g* back through the trocar 811 and out of the patient. Because the delivery tool is flexible, the delivery tool does not need to be perfectly aligned with the trocar to be removed and can bend slightly as needed to accommodate the usually tight spaces within the cavity. In the event any portion of the loop tie remains inside the cavity after cutting, the grasper may also be used to withdraw the loop tie.

In some embodiments, methods of repairing or treating a hernia repair includes the steps of: providing a sheet-tool assembly including an implantable sheet secured to a magnetic delivery tool via one or more loop ties extending from a bottom surface of the sheet and secured in a loop tie slot defined within the delivery tool; positioning an insertion member to a proximal end portion of the delivery tool; placing at least a distal end portion of the sheet-tool assembly into a channel defined within a rolling device; rotating the insertion member causing the sheet to roll onto itself around the delivery tool and within the channel of the rolling device to form a rolled sheet-tool assembly; inserting the rolled sheet-tool assembly through a trocar and into the abdominal cavity of a patient; positioning a magnetic positioner onto an outer surface of the patient's body directly above the abdominal cavity, and particularly with a first and second magnetic ends portions of the positioner located on opposite sides of the hernia, thereby causing magnetic members of the positioner and magnetic members of the delivery tool to magnetically engage with the sheet and the patient's body tissue therebetween; deploying and fixating the sheet to the tissue beneath and surrounding the hernia; removing the positioner from the outer surface of the patient; freeing the delivery tool from the sheet; and withdrawing the delivery tool from the patient.

It will be understood that various modifications may be made to the embodiments disclosed herein. Thus, those skilled in the art will envision other modifications within the scope and spirit of the disclosure.

What is claimed is:

1. A surgical kit for hernia repair comprising:
an implantable sheet;
a flexible delivery tool including an elongate body extending between a proximal end portion and a distal end portion, the proximal end portion of the delivery tool including a first magnetic member and the distal end portion of the delivery tool including a second magnetic member, wherein the implantable sheet and the flexible delivery tool are separable components; and,
a positioner including a handle extending between a proximal end portion and a distal end portion of the positioner, the proximal end portion including a first magnetic member and the distal end portion including a second magnetic member.

2. The surgical kit of claim 1, wherein the flexible delivery tool further includes a first loop tie slot defined within the proximal end portion of the flexible delivery tool.

3. The surgical kit of claim 2, wherein the first loop tie slot is positioned proximal to the first magnetic member on the proximal end portion of the flexible delivery tool, or alternatively wherein the first loop tie slot is positioned distal to the first magnetic member on the proximal end portion of the flexible delivery tool.

4. The surgical kit of claim 2, wherein the flexible delivery tool further includes a second loop tie slot defined within the distal end portion of the flexible delivery tool.

5. The surgical kit of claim 4, wherein the second loop tie slot is positioned proximal to the second magnetic element on the distal end portion of the flexible delivery tool, or alternatively wherein the second loop tie slot is positioned distal to the second magnetic element on the distal end portion of the flexible delivery tool.

6. The surgical kit of claim 5, wherein the flexible delivery tool further includes a first suture aperture defined within the proximal end portion of the flexible delivery tool, optionally wherein the flexible delivery tool further includes a second suture aperture defined within the distal end portion of the flexible delivery tool.

7. The surgical kit of claim 5, wherein the implantable sheet and the flexible delivery tool are preassembled to be connected to each other via a first and second loop tie, the first loop tie passing through and extending from a proximal end portion of the sheet, the first loop tie being positioned within the first loop tie slot positioned on a proximal end portion of the flexible delivery tool, and the second loop tie passing through and extending from a distal end portion of the sheet, the second loop tie being positioned within the second loop tie slot positioned on a distal end portion of the flexible delivery tool.

8. The surgical kit of claim 2, wherein the implantable sheet and the flexible delivery tool are preassembled to be connected to each other via a first loop tie passing through and extending from a proximal end portion of the sheet, the first loop tie being positioned within the first loop tie slot of the flexible delivery tool.

9. The surgical kit of claim 1, wherein at least one of the proximal or distal end portions of the flexible delivery tool further includes at least one crenulation extending outwardly therefrom, the at least one crenulation configured to engage openings in the implantable sheet when rolled.

10. The surgical kit of claim 1, wherein the first and second magnetic members of the positioner are complimentary to the first and second magnetic members of the delivery tool.

11. The surgical kit of claim 1, further comprising a rolling device, an insertion member, or both.

12. The surgical kit of claim 1, wherein the flexible delivery tool is unidirectional or alternatively wherein the flexible delivery tool is multidirectional and is configured to transition between a unidirectional configuration to a multidirectional configuration.

13. A delivery tool for an implantable sheet comprising:
a flexible rod including an elongate body extending between a proximal end portion and a distal end portion, the proximal end portion including a first magnetic member, the distal end portion including a second magnetic member, and at least one of the proximal or distal end portions including a loop tie slot defined therein, wherein the flexible rod is configured to be separable from the implantable sheet.

14. The delivery tool of claim 13, wherein the loop tie slot is generally L-shaped, or alternatively wherein the loop tie slot is sinusoidal.

15. The delivery tool of claim 13, wherein at least one of the proximal or distal end portions has a thickness greater than the elongate body, additionally or alternatively wherein at least of the proximal or distal end portions includes a loop suture extending from a suture aperture.

16. A method of repairing a ventral hernia comprising:
combining an implantable sheet, one or more loop ties, and a delivery tool to form a sheet-tool assembly, wherein the one or more loop ties secures the delivery tool to the implantable sheet,
preparing the sheet-tool assembly for insertion into a patient by combining the sheet-tool assembly with a rolling device and an insertion member to form a rolled sheet-tool assembly,
inserting the rolled sheet-tool assembly into a cavity of patient via a trocar using at least one of the rolling device or the insertion member,
positioning a positioner including a first and second magnetic member on an outer surface of the patient's body directly above the cavity, the first and second magnetic members of the positioner magnetically engaging a first and second magnetic members of the delivery tool inside the cavity to secure the implantable sheet therebetween and beneath the hernia;
deploying and fixating the implantable sheet to tissue surrounding the hernia;
removing the positioner from the outer surface of the patient's body;
freeing the delivery tool from the implantable sheet by removing the one or more loop ties from the implantable sheet, the delivery tool, or both; and
withdrawing the delivery tool from the patient.

* * * * *